US008331637B2

(12) United States Patent
Bar-Aviv et al.

(10) Patent No.: US 8,331,637 B2
(45) Date of Patent: Dec. 11, 2012

(54) SYSTEM AND METHOD OF AUTOMATIC PRIORITIZATION AND ANALYSIS OF MEDICAL IMAGES

(75) Inventors: Ezer Bar-Aviv, Tiberias (IL); Eliran Dahan, Haifa (IL); Zvi Devir, Haifa (IL)

(73) Assignee: Medic Vision-Brain Technologies Ltd., Haifa (IL)

( * ) Notice: Subject to any disclaimer, the term of this patent is extended or adjusted under 35 U.S.C. 154(b) by 1134 days.

(21) Appl. No.: 12/224,652

(22) PCT Filed: Feb. 18, 2007

(86) PCT No.: PCT/IL2007/000220
§ 371 (c)(1),
(2), (4) Date: Sep. 3, 2008

(87) PCT Pub. No.: WO2007/099525
PCT Pub. Date: Sep. 7, 2007

(65) Prior Publication Data
US 2009/0028403 A1 Jan. 29, 2009

Related U.S. Application Data

(60) Provisional application No. 60/778,383, filed on Mar. 3, 2006.

(51) Int. Cl.
*G06K 9/00* (2006.01)
(52) U.S. Cl. ........................ 382/128; 382/131
(58) Field of Classification Search .................. 382/128, 382/131
See application file for complete search history.

(56) References Cited

U.S. PATENT DOCUMENTS

| | | | |
|---|---|---|---|
| 6,385,332 B1 | 5/2002 | Zahalka et al. | |
| 6,892,089 B1 | 5/2005 | Prince et al. | |
| 6,978,039 B2 * | 12/2005 | Cline et al. | 382/128 |
| 7,646,899 B2 * | 1/2010 | Fitzpatrick | 382/128 |
| 2002/0141626 A1 | 10/2002 | Caspi | |
| 2002/0196965 A1 | 12/2002 | Wallace et al. | |
| 2003/0013951 A1 | 1/2003 | Stefanescu et al. | |
| 2003/0044055 A1 | 3/2003 | Park et al. | |
| 2004/0252870 A1 | 12/2004 | Reeves et al. | |
| 2005/0020903 A1 | 1/2005 | Krishnan et al. | |
| 2005/0283070 A1 | 12/2005 | Imielinska et al. | |
| 2006/0120584 A1 | 6/2006 | Hillman | |
| 2008/0240527 A1 * | 10/2008 | Keller | 382/128 |
| 2008/0292194 A1 * | 11/2008 | Schmidt et al. | 382/217 |

FOREIGN PATENT DOCUMENTS

WO   WO 2005/057498   6/2005

OTHER PUBLICATIONS

Machado et al ("Atlas Warping for Brain Morphometry", In SPIE Medical Imaging, Image Processing, pp. 642-651, 1998).*
International Preliminary Report on Patentability Dated Jan. 22, 2009 From the International Bureau of WIPO Re.: Application No. PCT/IL2007/000220.

* cited by examiner

*Primary Examiner* — Clayton E Laballe
*Assistant Examiner* — Leon W. Rhodes, Jr.
(74) *Attorney, Agent, or Firm* — Mark M Friedman

(57) ABSTRACT

A system for analyzing a source medical image of a body organ. The system comprises an input unit for obtaining the source medical image having three dimensions or more, a feature extraction unit that is designed for obtaining a number of features of the body organ from the source medical image, and a classification unit that is designed for estimating a priority level according to the features.

37 Claims, 13 Drawing Sheets

SYSTEM AND METHOD OF AUTOMATIC PRIORITIZATION AND ANALYSIS OF MEDICAL IMAGES

RELATED APPLICATIONS

This Application is a National Phase of PCT Patent Application No. PCT/IL2007/000220 having International filing date of Feb. 18, 2007, which claims the benefit of U.S. Provisional Patent Application No. 60/778,383 filed on Mar. 3, 2006. The contents of the above Applications are all incorporated herein by reference.

FIELD AND BACKGROUND OF THE INVENTION

The present invention relates to analysis of three-dimensional (3D) medical images and, more particularly, but not exclusively to automatic analysis of 3D medical images that depicts an organ or a human body system, especially the brain, or a section thereof by identified suspected indications of different diseases or disorders.

Systems and devices for visualizing the inside of living organisms are among the most important medical developments in the last thirty years. Systems like computerized tomography (CT) scanners and magnetic resonance imaging (MRI) scanners allow physicians to examine internal organs or areas of the body that require a thorough examination. In use, the visualizing scanner outputs a 3D medical image, such as a sequence of computerized cross-sectional images of a certain body organ, which is then interpreted by specialized radiologists.

Commonly, a patient is referred for a visual scan by a general practitioner or an expert practitioner. The 3D medical image is forwarded to and diagnosed by a general radiologist who is responsible for the analysis and diagnosis of the medical image. Radiologists are trained to deal with all kinds of medical images, such as those of the brain, abdomen, spine, chest, pelvis and joints. The medical images and the diagnosis thereof are sent back to the referring practitioner. It should be noted that there are private diagnostic imaging centers (DICs) that supply radiology imaging services to whoever is interested.

In most hospitals and radiology centers, the 3D medical images are transferred to a picture archiving communication system (PACS) before being accessed by the radiologists. The PACS is installed on one or more of computers, which are dedicated for storing, retrieving, distributing and presenting the stored 3D medical images. The 3D medical images are stored in an independent format. The most common format for image storage is digital imaging and communications in medicine (DICOM).

Generally, each radiologist receives a number of 3D medical images that are required to be interpreted and diagnosed within a certain period. The radiologist usually does not know in advance which patients are at greatest risk. Therefore, the sets of 3D medical images are usually diagnosed according to a first in first out (FIFO) scheme, indications given by the referring practitioners, a random order that has been determined by the radiologist or the clinic, or a combination thereof.

The time it takes to perform a diagnosis of a 3D medical image is important as delays in diagnosis of some pathology may have a direct effect on the therapy. Today, in a typical radiology division, a delay in the diagnosis of ambulatory patients can reach several hours or even days.

It should be noted that during the last decade, the number of diagnostic tests has increased by more than 150 percent. This increase reflects a delay in the diagnoses. A number of factors drive the increase.

Firstly, improved CT and MRI scan devices are performing scans faster than ever before. The acquisition time of each scan lasts only for a few fractions of a second and the image reconstruction time has decreased from more than five seconds per image to less than three seconds per image. When dealing with the large volume sets produced by CT and MRI, seconds often add up to minutes. By performing faster scans, the throughput of the scan devices has been increased resulting in a greater number of procedures performed in a set amount of time.

As the scan procedures are quickly performed, more scan procedures are performed in a set amount of time. One example of a technological development that increases the number of scan procedures per a set amount of time is the development of the electron beam tomography (EBT) scanner. The EBT scanner is a specific form of computed axial tomography (CAT or CT) in which the X-Ray tube is not mechanically spun in order to rotate the source of X-Ray photons. Although EBT can be used for a limited number of procedures, it has no throughput limitations as it has no moving parts and therefore no scan speed limitations.

Second, these diagnostic tests are used for more applications. For example, CT scans are now commonly used for trauma patients, cardiac patients and oncology patients as well as for other radiological purposes. The expansion in breadth of applications substantially broadens the utilization of CT scans, resulting in increased utilization of the scanner. Briefly stated, this increase is an outcome of the prevalence of the CT scanners and the expansion of CT scans to new medical fields and new diagnosis procedures. Another factor for such an increase is the technological progress. One technological development that has dramatically increased the number of performed CT scans is the introduction of the multi-slice CT device. The multi-slice CT device is based on revolutionary technology and considered one of the main drivers for future market growth. The multi-slice CT device comprises multiple rows of detectors that enable the acquisition of multiple slice images per gantry rotation. The multi-slice CT device increases the number of clinical diagnostic tests per unit time. The majority of multi-slice scanners offer an increase in both the number of slices and the thinness of slices, thereby reaching even closer to true volumetric scanning. The improved scan speed has resulted in a number of single-breath hold applications that could not historically be performed on CT scanners.

Another technological development that provides clinicians with the ability to perform new diagnostic tests is a combined positron emission tomography (PET)/CT scanner. The PET/CT scanner enables clinicians to detect tumors more accurately and pinpoint their exact location in the body as the highly sensitive PET scan picks up the metabolic signal of actively growing cancer cells in the body and the CT scan provides a detailed picture of the internal anatomy that reveals the size and shape of abnormal cancerous growths. The results of the PET/CT scans are to provide combined information on both the tumor location and the metabolism. Such combined information provides a more comprehensive point of view than the information that can be extracted separately from a PET scanner or a CT scanner. As a result, the PET/CT scanner can be used for extracting information for more applications than the commonly used CT scan or PET scan.

As the demand for medical imaging scans has increased, the installed base of CT scanners, MRI scanners, and CT/PET scanners respectively increased. For example, CT scan devices are now installed in more hospitals and freestanding imaging centers. Moreover, the number of mobile imaging services as well as cardiac and preventive screening centers that provide CT scan services has dramatically increased. It should be noted that the average number of CT scan devices in each installed base has also increased in the last decade.

As a result of the abovementioned reasons, the demand for radiologists substantially increases. Unfortunately, the supply of radiologists has not keep up with the demand and there is a growing shortage of several thousands in the number of well-trained, qualified radiologists only in the US.

During the last years, few developments have been conceived in order to increase the throughput of radiologists and in order to improve their diagnoses. Most of the developments are related to the field of computer aided detection (CAD) systems. CAD systems assist radiologists in detecting cancerous tissue after an initial diagnostic imaging screening procedure is performed. The CAD systems are used most often in mammography and recently in the diagnosis of lungs and intestine.

In practice, CAD is applied in the following fashion. A patient arrives at an imaging facility. A technologist uses imaging equipment to create medical images. These images are then forwarded to a CAD system. The CAD system analyzes the images and provides a visual representation of the images, marking potentially suspicious regions on a paper or an electronic display. Subsequently, when the radiologist is reading the images for the patient, the CAD outputs are examined in order to provide potential new areas for consideration. The utility of CAD is in prompting a radiologist to consider areas and specific region of interests (ROI) not initially detected in the first analysis of the images. Clearly, the CAD system is used as a tool intended to aid a radiologist in his or her diagnosis and not to replace them. Such tools are commonly known as second reader or second viewer. It should be noted that some CAD systems have been approved by the food and drug administration (FDA) to replace one physician in procedures that require diagnosis of two physicians.

Though the CAD system aids radiologists during the diagnosis process, the aforementioned throughput problems and the delays remain unchanged. Moreover, none of the known CAD systems is designed to aid in a general diagnosis of the brain.

Developments have been made in order to improve the workflow of radiologists using CAD systems. For example, Patent Application No. 2005/0123185A1 published on Jun. 9, 2005 describes such a method and a system. The method includes a number of steps: (a) accessing an image case, the image case comprises one or more digital images; (b) identifying a view orientation for each of the one or more digital images; (c) transmitting the image case to an algorithm server for processing of each of the one or more digital images to generate a CAD report for the image case; (d) providing a report system adapted to organize a plurality of CAD reports wherein each of the CAD reports are selectable by an operator for viewing; (e) automatically transmitting the CAD report to the report system; (f) allowing the operator to select the CAD report for viewing; and (g) displaying the selected computer aided detection report on the display.

Though such a system can improve the workflow, the delays in the diagnosis process are not substantially decreased, inter alia, because the order of the received 3D medical images remains constant.

Other known CAD systems are usually designed to aid radiologists in the diagnosis of mammographic images. For example, Patent Application No. 2006/0222228A1 published on Oct. 5, 2006 describes a method and system adapted to analyze a radiograph for bone mineral density screening and mammography computer aided detection. The method for analyzing a radiograph includes the following steps: providing a digital image based on the radiograph; determining whether a radiographic absorptiometry analysis or computer aided detection analysis is desired; and performing a radiographic absorptiometry analysis or computer aided detection analysis on the digital image based on the desired determination. The system can include an input station, a report station, and a printer.

Though such CAD systems improve the quality of each analysis, they fail to improve the throughput of the diagnosis. Moreover, most of the known CAD systems are designed to aid radiologists in diagnosis of mammographic images or other indication-specific images, and some of the known CAD systems are designed for other market segments. Examples for such market segments are chest-lung diagnosis and virtual colonoscopy diagnosis.

Though aiding in the detection process, the currently used CAD systems do not overcome the difficulties in the current diagnosis workflow of medical images. Moreover, the currently used CAD systems do not aid in the detection of indications in some market segments such as brain MRI scans, brain CT scans etc.

There is thus a widely recognized need for, and it would be highly advantageous to have, a system and a method for overcoming the aforementioned difficulties devoid of the above limitations.

SUMMARY OF THE INVENTION

According to one aspect of the present invention there is provided a system for analyzing a source medical image of a body organ. The system comprises an input unit for obtaining the source medical image, the source medical image having at least three dimensions. The system further comprises a segmentation unit for segmenting the source medical image by matching with a reference medical image of a respective normal organ, the reference medical image already being segmented and the reference medical image having at least three dimensions. The system further comprises a feature extraction unit for obtaining a plurality of features of the body organ from the segmented source medical image and a classification unit for estimating a priority level for the source medical image according to the features.

Preferably, the priority level is a normality which is calculated according to the features.

Preferably, the source medical image is a member of the following group: computerized tomography (CT) scan images, magnetic resonance imager (MRI) scan images, and positron emission tomography (PET)-CT scan images.

Preferably, the body organ is a member of the following group: a plurality of body organs, a human body system, a section of a human body system, an area in the body, and a section of a body organ.

Preferably, the system further comprises a collaboration module having a repository of reference images of reference normal organs, the collaboration module being configured to choose the reference medical image from the repository.

More preferably, each one of the reference medical images depicts a reference normal organ being associated with a different group of patients, the matched reference and source images depicts an organ a patient from at least one common group.

More preferably, the different group of patients comprises patients from one of the following group: a common age group, a common gender group, a common physical condition group, and a common race group.

Preferably, the features are obtained according to differences between the body organ and the reference normal organ.

Preferably, the system further comprises a registration module being configured for performing a spatial image registration according to spatial positioning differences between the body organ and the reference normal organ, the spatial positioning differences being used during by the segmentation unit for the segmenting.

More preferably, the registration module comprises a global motion sub-module being configured for estimating a global motion vector according to the spatial positioning differences, the global motion vector being used during the spatial image registration.

More preferably, the registration module comprises a 3D affine transformation sub-module being configured for estimating an affine transformation vector according to the spatial positioning differences, the affine transformation vector being used during the spatial image registration.

More preferably, the reference medical image is associated with a plurality of reference descriptors, the 3D affine transformation sub-module being configured for identifying a plurality of source descriptors in the source medical image the, the spatial positioning differences being determined according to spatial positioning differences between the reference and source descriptors.

More preferably, the reference descriptors and the source descriptors are local extrema voxels in the reference medical image and the source medical image respectively.

More preferably, the registration module comprises an optic flow sub-module, wherein the optic flow sub-module is configured for estimating a spatial optic-flow field according to the spatial positioning differences, the optic-flow field being used during the spatial image registration.

More preferably, each the reference medical image is associated with a segmented reference image, the segmented image define a plurality of reference segments in the reference normal organ.

More preferably, the segmentation unit is configured to segment the source medical image according to the segmented reference image.

More preferably, the segmentation unit is configured for identifying a plurality of source segments in the source medical image, wherein each the source segment matches a respective reference segment of the plurality of reference segments.

Preferably, the segmentation unit generates the segmented source medical image by matching voxels of the reference medical image with voxels of the source medical image.

More preferably, the source segments are used for identifying the features.

More preferably, the system further comprises an active contour (AC) module, the segmentation unit being configured to forward the plurality of source segments to the AC module, the AC module being configured to refine the source segments according to the source medical image.

More preferably, the AC module being configured to refine the source segments according to respective reference segments.

More preferably, each the respective reference segments is configured according to at least one prior-knowledge about a member of the following group: a shape, a color, and a size of a related segment in the body organ.

More preferably, the refinement is performed according to the Hounsfield unit (HU) values of voxels of the source segments.

Preferably, the classification unit is configured for labeling the source medical image with the priority level.

Preferably, the classification unit is configured for labeling the source medical image with a certainty level that reflects the estimated accuracy of the priority level.

Preferably, the classification unit is configured for alerting a user if the priority level is above a predefined threshold.

Preferably, the priority level is used for prioritizing the source medical image in respect to a plurality of other source medical images having respective priority levels.

Preferably, the priority level is used for updating a working list of a plurality of source medical images, the working list being arranged according to respective priority levels of the plurality source medical images.

More preferably, the working list is forwarded to a member of the following group: a picture archiving and communication system (PACS), a central server, and a working station.

More preferably, at least one of the features is calculated according to the volume of an area of the body organ in relation to a respective volume of a respective area in the reference normal organ.

More preferably, at least one of the features is calculated according to the center-of-mass of an area of the body organ in relation to a respective center-of-mass in a respective area in the reference normal organ.

More preferably, at least one of the features is calculated according to second order moments of an area of the body organ.

Preferably, at least one of the features is calculated according to the surface area of an area of the body organ in relation to a respective surface area in a respective area in the reference normal organ.

Preferably, at least one of the features is calculated according to the average color of voxels in an area of the body organ.

Preferably, at least one of the features is calculated according to one or more characteristics of the shape of an area of the body organ in relation to a respective one or more characteristics of the shape of a respective area in the reference normal organ.

More preferably, the one or more characteristics are estimated according to a spherical Fourier transform.

More preferably, one or more characteristics are estimated according to a predefined curvature.

Preferably, at least one of the features is calculated according to the global motion in an area of the body organ in relation to the positioning of the reference normal organ.

Preferably, at least one of the features is calculated according to hyperdense/hypodense areas in an area of the body organ.

Preferably, at least one of the features is calculated according to the symmetry between at least two areas of the body organ.

Preferably, the body organ is a depicted human brain.

More preferably, at least one of the features is calculated according to the uniformity of a skull that being depicted in the source medical image.

More preferably, at least one of the features is calculated according to the ratio between the measures of ventricles depicted in the source medical image.

More preferably, at least one of the features is calculated according to the volume of a cerebrospinal fluid (CSF) in an upper temple depicted in the source medical image.

More preferably, at least one of the features is calculated according a minimum mean square error between the reference and source medical images.

More preferably, at least one of the features is calculated according an More preferably, at least one of the features is calculated according an estimation of cerebrospinal fluid of in a sub-arachnoid's space in the depicted human brain.

Preferably, at least one of the features is calculated according to the existence of predefined structures in the segmented source medical image, the existence is determined by matching segments of the segmented source medical image with a set of normal segmentation structures.

Preferably, at least one of the features is calculated according a distance between segments in the segmented source medical image.

Preferably, at least one of the features is calculated according to the existence of predefined structures in the segmented source medical image, the existence is determined by matching segments of the segmented source medical image with a set of normal segmentation structures.

More preferably, at least one of the features is calculated according an estimation of the existence of a cerebral aneurysm in the depicted human brain, the estimation is based on volume and curvature measurements of segments of the segmented source medical image.

More preferably, at least one of the features is calculated according to the positioning of a middle symmetry line that bisects the depicted human brain to left and right sides.

More preferably, at least one of the features is calculated according to a mean color of at least one area in the source medical image.

More preferably, at least one of the features is calculated according to a diversion level of the midsagittal plane (MSP) depicted in the source medical image.

More preferably, the diversion level is based on the symmetry level of the MSP.

More preferably, at least one of the features is calculated according to a symmetry value, the symmetry value being calculated by measuring the size of at least one portion of at least one hemisphere depicted in the source medical image.

More preferably, at least one of the features is calculated according to a distance between at least two temporal horns depicted in the source medical image.

Preferably, the classification unit further comprises a diagnosis module, the diagnosis module being configured for generating a diagnosis report according to the features.

Preferably, the input unit comprises a preprocessing module, the preprocessing module being configured for preprocessing the source medical image.

Preferably, the input unit is operatively connected to a Picture archiving and communication system (PACS), the input unit being configured to receive the source from the PACS.

Preferably, the input unit is operatively connected to a medical imaging device, the input unit being configured to receive the source from the medical imaging device.

Preferably, the input unit being configured for receiving a digital imaging and communications in medicine (DICOM) object, the input unit being configured for extracting the source image from the DICOM object.

Preferably, the source medical image is associated with medical data, wherein at least one of the features being generated according to the medical data.

Preferably, the input unit is configured to receive the source medical image from a member of the following group: a CD reader, a DVD reader, the Internet, a computer network, a hard disk, a digital imaging and communications in medicine (DICOM) object reader and a portable memory.

Preferably, the classification unit comprises at least one classifier, the at least one classifier being configured to classify the source medical image according to the features, the classification being determined according to the at least one classifier.

According to another aspect of the present invention there is provided a method for analyzing a source medical image of a body organ. The method comprises the following steps: a) receiving the source medical image, b) segmenting the source medical image by matching with a reference medical image of a normal organ already segmented, c) obtaining information about features in the body organ from the segmented source medical image, and d) estimating a priority level for the source medical image according to the information.

Preferably, the segmenting is done by matching between voxels of the source medical image and voxels of the reference medical image.

Preferably, the method further comprises a step of labeling the source medical image according to the priority level.

Preferably, the source medical image is a member of the following group: a set of computerized tomography (CT) scan images, a set of a magnetic resonance imager (MRI) scan images, and a set of a positron emission tomography (PET)-CT scan images.

Preferably, the body organ is a member of the following group: a plurality of body organs, a human body system, a section of a human body system, and a section of a body organ.

Preferably, the method further comprises a step a1) between step a) and b) of choosing the reference medical image from a plurality of reference images repository, each the reference image depicts a reference normal organ, the obtaining of step b) is based on differences between the body organ and the reference normal organ.

More preferably, each the reference normal organs is associated with a different group of patients.

More preferably, the different group comprises one of the following group: an age group, a gender group, a physical condition group, race group, and a combination thereof.

More preferably, the method further comprises a step a1) between step a) and b) of performing a spatial image registration according to spatial positioning differences between the body organ and the reference normal organ.

More preferably, the performing of step a1) comprises estimating a global motion vector according to the spatial positioning differences, the spatial image registration being done according to the global motion vector.

More preferably, the performing of step a1) comprises estimating an affine transformation vector according to the spatial positioning differences, the spatial image registration being done according to the affine transformation vector.

More preferably, the performing of step a1) comprises estimating a spatial optic-flow field according to the spatial positioning differences, the spatial image registration being done according to the optic-flow field.

More preferably, each the reference medical image is associated with a segmented reference image that define a plurality of reference segments in the reference normal organ, wherein the segmenting of step b) comprises a step of identifying a plurality of source segments in the source medical image, each the source segment match a respective reference segment of the plurality of reference segments.

More preferably, the segmenting further comprises refining the source segments according to the source medical image.

More preferably, the refining is performed according to the Hounsfield unit (HU) values of voxels of the source segments.

More preferably, the method further comprises a step of alerting a user if the priority level is above a predefined threshold.

Preferably, the priority level is used for prioritizing the source medical image in respect to a plurality of other source medical images having respective priority levels.

More preferably, at least one of the features is calculated according to the volume of an area of the body organ in relation to a respective volume of a respective area in the reference normal organ.

More preferably, at least one of the features is calculated according to the center-of-mass of an area of the body organ in relation to a respective center-of-mass in a respective area in the reference normal organ.

More preferably, at least one of the features is calculated according to second order moments of an area of the body organ.

More preferably, at least one of the features is calculated according to the surface area of an area of the body organ in relation to a respective surface area in a respective area in the reference normal organ.

More preferably, at least one of the features is calculated according to the average color of voxels in an area of the body organ.

More preferably, at least one of the features is calculated according to one or more characteristics of the shape of an area of the body organ in relation to respective one or more characteristics of the shape of a respective area in the reference normal organ.

More preferably, at least one of the features is calculated according to hyperdense/hypodense areas in an area of the body organ.

More preferably, at least one of the features is calculated according the symmetry between at least two areas of the body organ.

More preferably, the estimating comprises a step of generating a diagnosis report according to the features.

More preferably, the method further comprises a step between steps a) and b) of preprocessing the source medical image.

More preferably, the source medical image is received from a Picture archiving and communication system (PACS).

More preferably, the source medical image is associated with medical data, wherein at least one of the features is generated according to the medical data.

More preferably, the features are represented in a feature vector, the feature vector being used for the estimation.

According to another aspect of the present invention there is provided a system for prioritizing a plurality of source medical images. The system comprises an input unit for obtaining the plurality of source medical images, each the source medical image depicting an organ, an analysis unit for analyzing the source medical images, and a prioritizing unit for estimating a priority level for each of plurality of source medical images according to the respective analysis, wherein the plurality of source medical images are prioritized according to the priority levels.

Preferably, the organ is the brain.

According to another aspect of the present invention there is provided a learning system for updating a unit for analyzing medical images. The learning system comprises an input unit for obtaining a medical image of an organ and a related diagnosis, a feature extraction unit configured for obtaining a plurality of features of the organ from the medical image, a training set configured for using the features and the related diagnosis for generating a classification of the medical image, and a learning module configured for generating a classifier according to the classification.

Preferably, the learning unit further comprises an image repository configured for storing the medical image in association with the classification.

Preferably, the learning module is configured for generating the classifier according to a number of medical images and respective the classifications from the image repository.

According to another aspect of the present invention there is provided a system for analyzing a source medical image of a body organ. The system comprises an input unit for obtaining the source medical image having at least three dimensions, a feature extraction unit for obtaining a plurality of features of the body organ from the source medical image, and a classification unit for estimating a priority level for the source medical image according to the features.

Preferably, the priority level is chosen from at least three predefined priority levels.

Preferably, the classification unit comprises a diagnosis module for generating a diagnostic report according to the features.

Preferably, the diagnostic report describes pathological indications that appear in the body organ.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
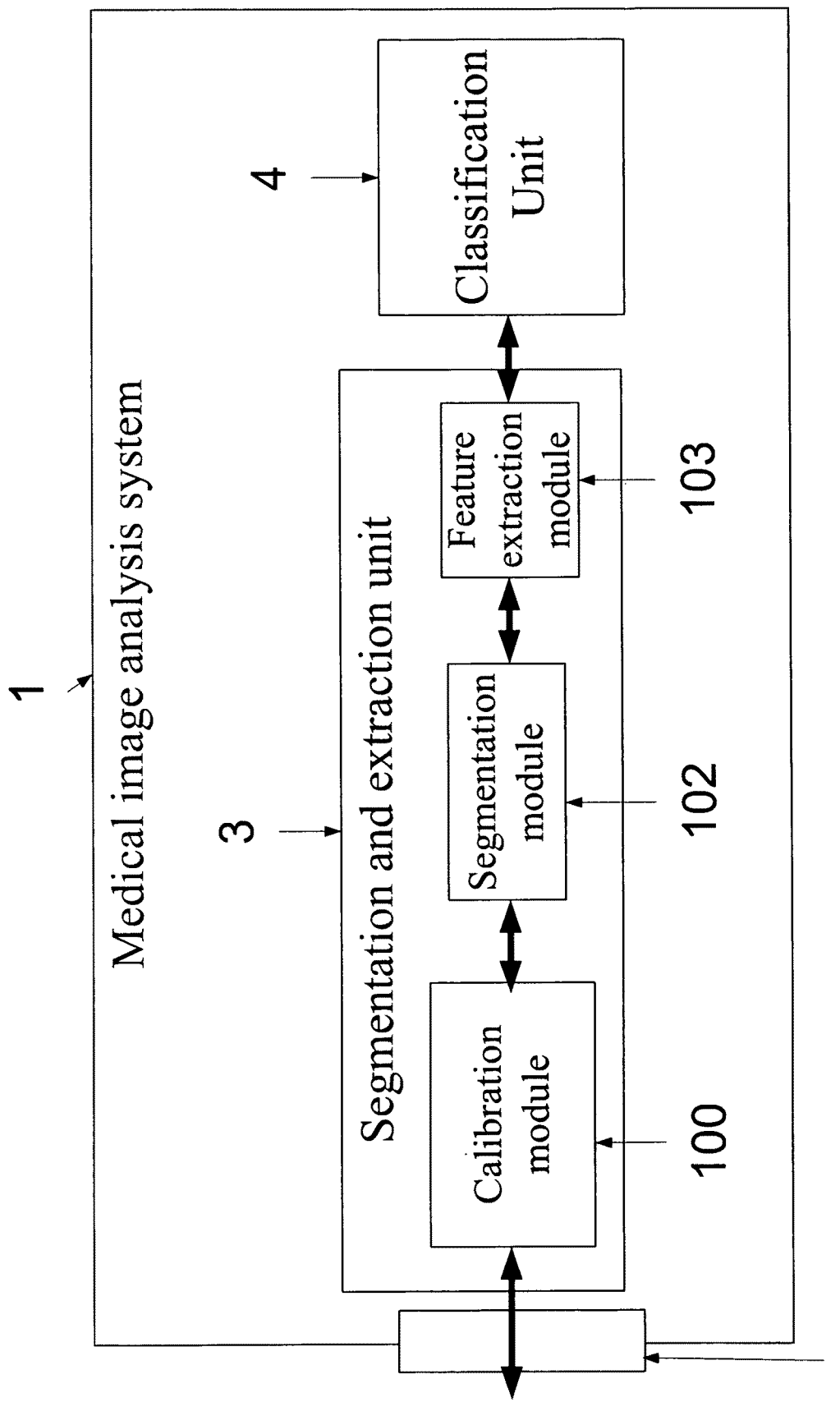
FIG. 1 is a schematic illustration of a medical image analysis system, according to a preferred embodiment of present invention.

The present embodiments comprise a real-time autonomous prioritization and alerting system for 3D medical images, such as CT scans. The system provides a solution for a number of problems, inter alia, the shortage in radiologists and the critical period between the carrying out of a CT scan and the diagnosis thereof. The system receives a 3D medical image, analyzes it, and preferably alerts when pathology is found. Preferably, the system gives the 3D medical image a priority-level that indicates the urgency of the case. Preferably, the system is used for analyzing and prioritizing a number of 3D medical images. The priority level of each one of the 3D medical images allows, inter alia, prioritization of the scans which are pending on the working station, therefore allowing the radiologist to diagnose critical cases first. In addition, the system enhances the radiologists' throughput in two or more levels. First, the system extracts high-probability normal cases from the queue of pending 3D medical images, allowing radiologists review pending 3D medical images that have been estimated as pathological first. Second, the system marks suspicious areas, which may be referred to as regions of interest (ROIs) in the pending 3D medical images, allowing radiologists to spend less time diagnosing each case.

According to one aspect of the present invention there is provided a system and a method for analyzing and classifying a received 3D medical image. The analysis and classification is performed by extracting a set of features, which are preferably arranged in a features vector, from the 3D medical image and evaluating the normality level of the features vector. The features vector extraction process is preferably based on segmentation of the received 3D medical image which have been identified using segmentation of a 3D reference medical. The 3D reference medical image is chosen from a database that comprises a number of reference records.

Considering the database, each one of the reference records is designated to be matched with 3D medical images taken from a certain group of patients, as further described below. In order to allow such a matching, the 3D reference medical image and the received reference medical image are correlated in an image registration process. Such a correlation allows the extraction of the features in a more accurate and efficient manner, as described below. Preferably, the extracted features are used for classifying or prioritizing the received 3D medical image. In such a manner, a radiologist receives a priority level of the organ depicted in the received 3D medical image that he or she has to diagnose along with a comprehensive overview of some of the features that support the findings. In one embodiment, if the priority level is high, the system alarms the radiologist or any other system user.

The principles and operation of an apparatus and method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. In addition, it is to be understood that the phraseology and terminology employed herein is for the purpose of description and should not be regarded as limiting.

A 3D medical image, a spatial image, or, a reference image, a segmented image, and a source image may be understood as a sequence of CT scan images, a sequence of MRI scan images, a sequence of PET-CT scan images, or as a 3D medical image with additional layers, a DICOM object, etc.

A medical imaging system may be understood as an MRI imaging system, a CT imaging system, a PET-CT imaging system, etc.

A communication network and computer network may be understood as the Internet, an Ethernet, a local area network, a public switched telephone network (PSTN), a virtual private network, a wireless network, a cellular communication network, etc.

An organ may be understood as human body organ, a human body system, an area of an organ, a number of areas of an organ, a section of an organ, a section of a human body system, etc.

Reference is now made to FIG. 1, which is a schematic illustration of a medical image analysis system 1, according to a preferred embodiment of present invention. The medical image analysis system 1 comprises an input unit 2 for obtaining spatial medical images, a segmentation and extraction unit 3 having a number of modules, and a classification unit 4.

The input unit 2 is designed to receive source images either directly from a medical imaging system or indirectly via a content source such as a PACS server, a PACS workstation, a computer network, or a portable memory device such as a DVD, a CD, a memory card, etc. Each source image is preferably associated with medical information needed for the feature extraction and classification process, which are described below. Such medical information may comprise the patient age, gender, medical condition, ID, etc. Other important features such as 3D affine transformation descriptors may also be associated with the source image, as further described below. Such medical information is associated to a certain source image. The input unit 2 is adapted to interface with one or more content sources.

Preferably, the input unit 2 is designed to preprocess the received source image and to forward it to the segmentation and extraction unit 3. Preferably, the source image is preprocessed according to the requirements of the feature extraction process. In one embodiment, the source image is denoised and enhanced using commonly known edged preserving filters such as Beltrami filter or bilateral filter.

The segmentation and extraction unit 3 is designed to receive the source image from the input unit 2 and to generate based thereupon a feature vector (FV) consisting of a number of features extracted from the source image and useful for prioritizing the image. The segmentation and extraction unit 3 comprises a collaboration module 100, which is used to provide a reference 3D medical image of a segmented normal organ to the received source image, and a segmentation module 102, which is used to segment the source image according to segmentation of the normal organ in the reference 3D medical image. The segmentation is preferably performed by mapping voxels of the source image to respective voxels in the reference 3D medical image. As the reference 3D medical image has already been segmented, the voxels in the source image are automatically assigned to the sub-structure of the voxel they are mapped to. The segmentation and extraction unit 3 further comprises a feature extraction module 103 that is used to generate the FV according to segments in the source image.

In one embodiment, the FV includes not only information extracted from the image but also information about the patient. This may include medical information about the related patient provided by doctors involved at the imaging stage, or taken from the patient's medical records, as further described below. It should be noted that such medical information may comprise clinical diagnosis about the related patient. For example, the medical information describes whether the related patient suffers from dizziness, hearing injuries, hearing difficulties, paralysis, weakness, headache, sickness, vomiting, etc.

The feature extraction module 103 generates the FV according to a match between the segments in the source image and segments in the reference image, as described below.

The classification unit 4 is designed to receive the FV and to estimate accordingly a priority level that is related to the received source image. Preferably, the classification unit 4 comprises a number of classifiers that are designed to evaluate the received FV. Based on the matching, as described below, the classification unit 4 is designed to alarm a system operator or to generate a classification report. As further described below, the classification report includes medical information, such as pathological indications that have been labeled by the segmentation and extraction unit 3 and classified by the classification unit 4. In one embodiment of the present invention, the information, which is designated for the classification report, is fed into a related DICOM object or used for generating a new DICOM object. Preferably, the medical information is fed as respective identifiers of the DICOM object and the features are added to the source image in an overlaying layer or in a designated list. Preferably, the classification unit 4 is connected to a diagnosis unit (not shown) which is designed to receive the outputs of the classification units and to generate automatically, based thereupon, a diagnosis report. The diagnosis report is generated according to different pathological indications, which are indicated by the FV, and the classification thereof. Preferably, the diagnosis report is presented on a user interface such as a display device.

Figure 2:
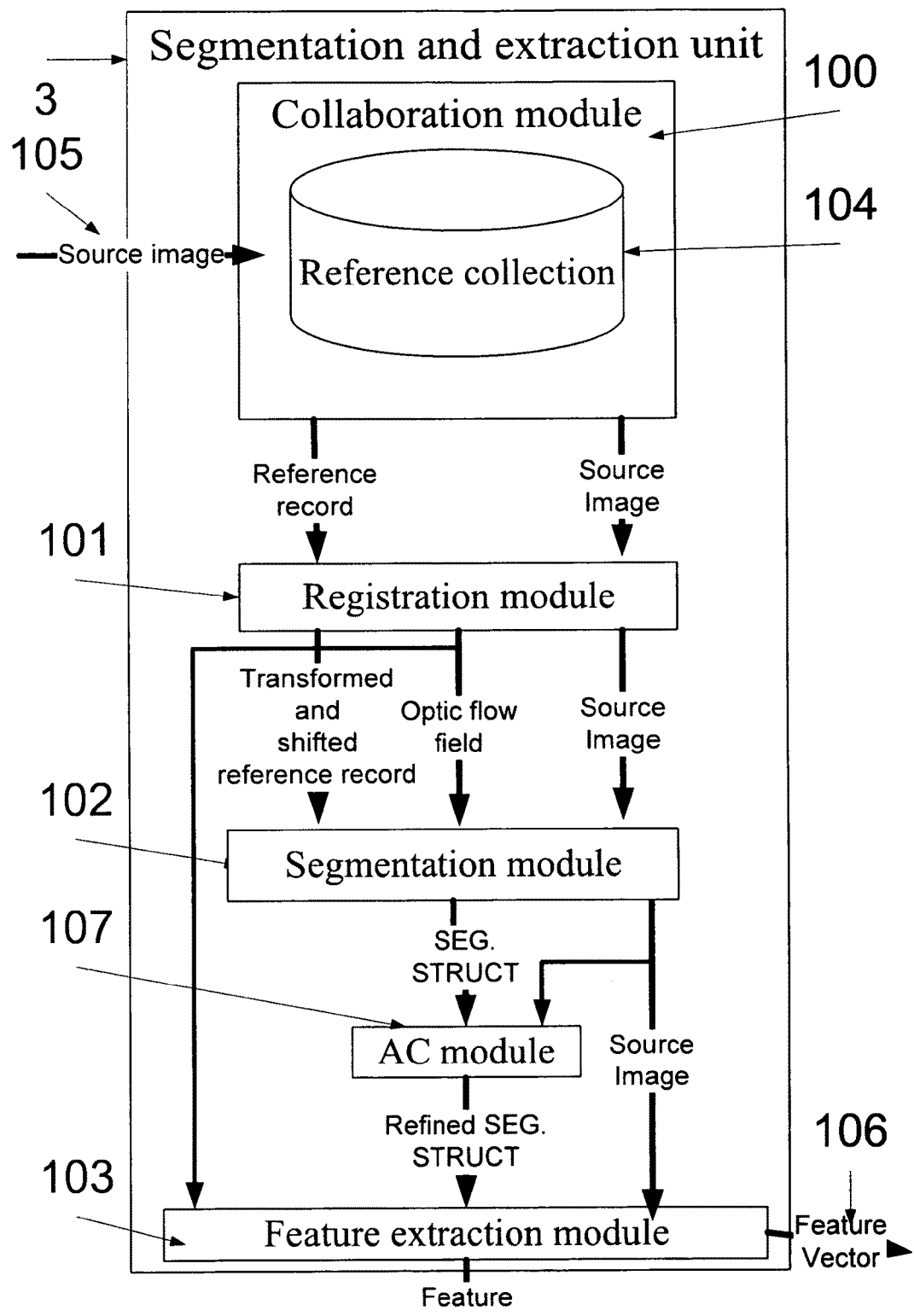
FIG. 2 is a schematic illustration of a feature extraction unit and modules thereof, according to a preferred embodiment of present invention.

Reference is now made to FIG. 2, which is a schematic illustration of the segmentation and extraction unit 3 that is depicted in FIG. 1, according to a preferred embodiment of present invention. The segmentation and extraction unit 3 comprises an input 105 for receiving the source image from the input unit, a calibration module 100 that comprises a reference collection 104, a registration module 101, a segmentation module 102, a feature extraction module 103, and an output 106 for outputting the FV to the classification unit (not shown), as described below.

In use, the segmentation and extraction unit 3 receives, via the input 105, the source image, which is directly forwarded to the calibration module 100. As depicted in FIG. 2, the calibration module 100 comprises a reference collection 104. The reference collection 104 comprises a number of reference records. Each reference record comprises a reference-image and a segmented-image, which are described below. Preferably, each one of the reference records is associated with a list of 3D affine transformation descriptors for the adaptation process that is described below, in relation to FIG. 6. The calibration module 100 facilitates the matching, which is performed by the registration and segmentation modules 101, 102, by choosing a reference record that is suitable for the received source image. The reference record may be chosen according to inputs of the system user, which are received via a designated user interface that is connected to the medical image analysis system 1, or automatically according to medical information that is associated to the received source image, as described above.

Each one of the reference images depicts a typical representation of an organ, such as a typical brain, which is associated with a different group of patients. For example, in one embodiment of the present invention, some or all the reference records comprise a reference image that depicts a typical brain of individuals of a certain age group, such as babies, children, adults or elderly. The reference records may be divided according to different characteristics, such as age groups, gender groups, physical condition groups, race groups, etc. and the combination thereof.

A reference record is preferably chosen according to the characteristics of the patient whose organ is depicted in the received source image as such suitability improves the detection of pathological indications in the received 3D medical image in subsequent steps. By choosing a suitable reference record, certain causes of faulty diagnosis can be avoided. Such faulty diagnoses occur as the same pathology may have different indications and expressions in patients from different groups and as the same indications may indicate different pathologies for patients with different characteristics, such as age, gender, physical condition, race, etc. For example, it is commonly known that brain measures of cognitive function brain structure and brain neurochemistry have age-related changes. Structural imaging studies with CT and magnetic resonance images have shown progressive age-associated increases in ventricular and sulcal cerebrospinal fluid (CSF) and associated declines in cerebral hemispheric and gray matter volumes, involving differences in both cortical and subcortical structures, see Murphy D G M et al, *Age-related differences in volumes of subcortical nuclei, brain matter, and cerebrospinal fluid in healthy men as measured with MRI, Arch Neurol* 1992; 49:839-845 and Coffey C E et al, *Quantitative cerebral anatomy of the aging human brain, Neurology* 1992; 42:527-536. While increases in the ventricular and the CSF and associated declines in cerebral hemispheric and gray matter volumes are common in the elderly patients and not considered as pathological phenomena, they may be considered pathological and less common in younger patients.

It should be noted that the reference images and preferably the related segmented-images are defined to be matched with the received source image. Therefore, if the received source image is a CT image, the reference image and the related segmented-image are defined to be matched which a CT image etc. Preferably, the reference collection 104 comprises a number of reference images and related segmented-images that depict the same organ, for the same group of patient, wherein each pair of reference image and related segmented-image is designed to be matched with a source image from a different medical imaging scanner.

Preferably, reference images may be chosen to depict different groups of patients according to a number of criteria, such as age and sex. Such segmentation may be important if there is a correlation between the division into groups and pathological indications criteria. For example, in the brain, sex-related changes in the degree of age-associated brain atrophy have been described. Men have earlier increases in ventricular volume than women, as measured with CT, but the increments in women are somewhat faster once they are observable, see Takeda S et al., *Age-related brain atrophy, J Gerontol* 1985; 40:159-163. *MRIa steeper age-associated increments of sulcal CSF and more severe left hemisphere atrophy were found in men*, see Gur R C et al., *Proc Natl Acad Sci USA* 1991; 88:2845-2849.

Each reference record includes a reference-image, such as a normal and high resolution CT scan, and a corresponding segmented-image.

The segmented-image is preferably a segmented replication of the reference-image or an array of segmentation maps, each depicts a contour of a certain area or a segment in the depicted organ. Each voxel in the segmented-image is given with a value that represents an area in the organ that is depicted in the reference image. It should be noted that the term organ is also used to describe a number of organs, a human body system, or a section thereof, as defined above.

In such a manner, various organs, tissues, and structures of the organ are marked and tagged. For example, if the organ is a human brain, all the voxels that depicts the left ventricle are marked with the value X and all the voxels that depicts the cerebrospinal fluid are marked with the value Y. Preferably, the segmented-images are generated according to the instructions of an expert physician or a team of expert physicians.

Preferably, the calibration module 100 is designed to choose a reference record according to an input from a user interface that is connected to the system, or according to information which is assimilated into the source image, such as the age and sex of the patient, as described above. The reference and source images are forwarded to the registration module 101.

Figure 3:
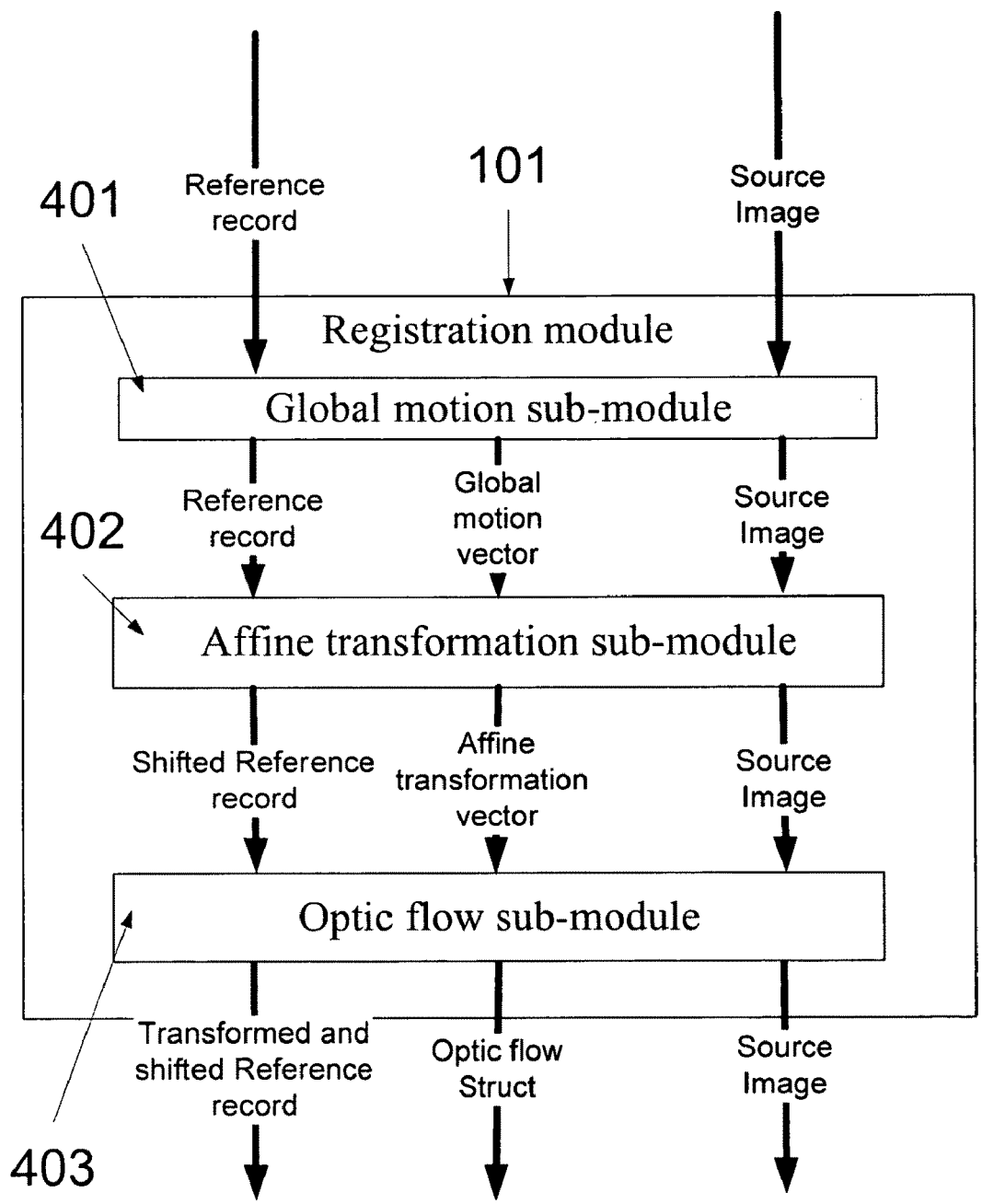
FIG. 3 is a schematic illustration of a registration module and sub-modules thereof, according to a preferred embodiment of present invention.

Reference is now made to FIG. 3, which is a schematic illustration of the registration module 101 that is depicted in FIG. 2, according to a preferred embodiment of the present invention. The registration module 101 comprises three sub-modules 301, 302, and 303. The registration module 101 is designed to adjust the reference image according to the source record. Such an adjustment is used to facilitate accurate identification of pathological indications in the source image as well as identification of the various structures within the source image. The adjustment is preferably performed by three sub-modules. The first sub-module 401, which may be called the global motion sub-module, is designed to find a global motion vector that correlates between the source and the reference images. This module outputs a global motion vector that allows the setting of the reference image on the same grid with the source image. The adjusting of the reference image according to the global motion vector allows the generation of a shifted reference image that has a common grid origin with the source image.

The second sub-module 402, which may be called the 3D affine transformation sub-module 402, is designed to find an affine transformation matrix that correlates between the source and the shifted reference images. The affinity matrix allows the performance of an affine transformation on the shifted reference image that allows the generation of a transformed and shifted reference image, which is better correlated with the source image than the shifted reference image, as described below. The transformed and shifted reference image is a scaled, rotated, and translated version of the shifted reference image. The affine transformation preserves the collinearity and the ratios of distances of the shifted reference image.

The third sub-module 403, which may be called the optic-flow sub-module 403, is designed to find an optic-flow field that correlates between each voxel in the source image and a respective voxel in the transformed shifted reference image. This module outputs a 3D array that allows the generation of a version of the transformed shifted reference image in which each voxel has been associated with a respective voxel in the source image. For clarity, the version of the transformed shifted reference image that has been adjusted according to the optic-flow field is called a registered reference image.

The global motion sub-module 401 generates a motion vector, according to a 3D image registration algorithm, that can be used to adjust the source image. In such an embodiment, the source image and the reference image of the chosen reference record are transformed into a common coordinate system.

Figure 4:
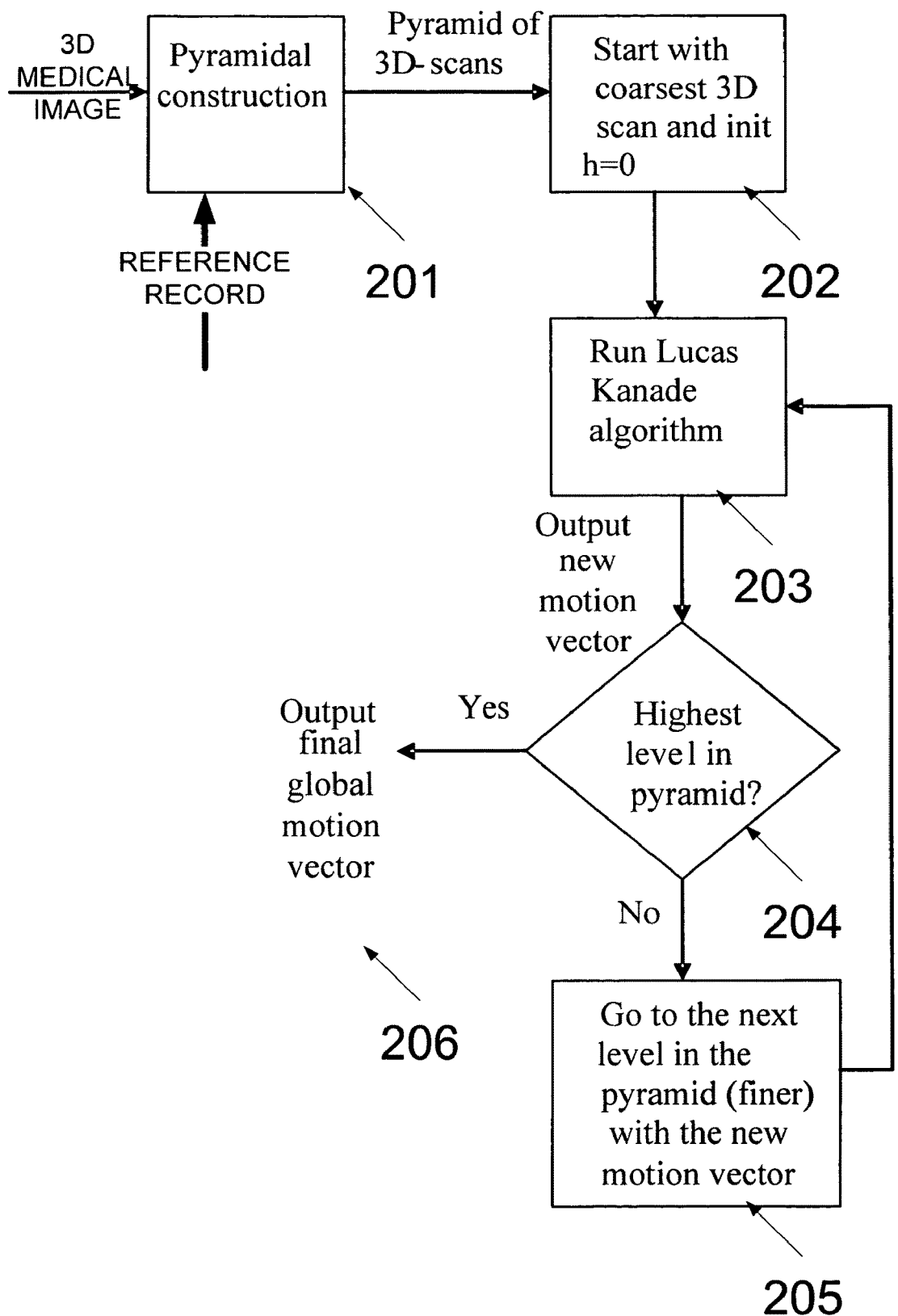
FIG. 4 is a flowchart of a global motion vector generation process that is performed by the global motion sub-module of the registration module, according to a preferred embodiment of present invention.

Reference in now made to FIG. 4, which is a flowchart of a global motion identification process that is made by the global motion sub-module, according to a preferred embodiment of the present invention. FIG. 4 depicts steps of the global motion identification process, which is based on a variant of the Lucas-Kanade global-motion algorithm, see D. Lucas et al, *An Iterative Image Registration Technique With an Application to Stereo Vision, Proc 7th International Joined Conference on Artificial Intelligence (IJCAI)*, 1981 Aug. 24-28, Vancouver, British Colombia, pp. 674-679, which is incorporated in its entirety by reference into the specification.

During an image registration process, a 3D global motion vector $V = \vec{h} \in R^3$, which is also known as the disparity vector, is calculated. The motion vector is calculated according to two functions $F(\vec{x})$ and $G(\vec{x})$, each respectively gives values of a certain voxel at location x in the received 3D medical image and in the reference image of the chosen reference record respectively. The 3D global motion vector minimizes some measure of the difference between $F(\vec{x} + \vec{h})$ and $G(\vec{x})$, for x in the same region.

As the global motion vector is calculated between two 3D images, a pyramidal implementation of the Lucas-Kanade algorithm with a global-motion of a constant field is used.

During the global motion vector generation process, a 3D-pyramid of the received 3D medical image f($\vec{x}$), which is preferably a CT scan, is built. As described below, in such an implementation, the Lucas-Kanade algorithm is separately applied to each layer in the pyramid. The output of the Lucas-Kanade algorithm in each layer is transferred to the next layer in the pyramid, serving as an initial condition for the calculated global motion in the layer. We start with the coarsest reference image and $\vec{h}=0$ and continue to finer versions of the reference image until we reach the source record.

For clarity, A denotes the source image, B denotes the reference image of the reference record, H denotes a coarse grid on which B and A are compared, A(x, y, z) denotes a 3D array of the received source image, [hx', hy', hz'] denotes the intervals of a grid on which A is defined, B(x, y, z) denotes a 3D array of the reference record, and [hx, hy, hz] denotes B's intervals of a grid on which B is defined. During the pyramidal implementation of the Lucas-Kanade algorithm, a disparity vector is identified. The disparity vector, denoted by $V=[v_x, v_y, v_z]$ minimizes some measures of the differences between A and B as it defines the minimum mean square error (MSE) between $$B\left(v_x + x \cdot \frac{hx'}{hx}, v_y + y \cdot \frac{hy'}{hy}, v_z + z \cdot \frac{hz'}{hz}\right)$$

and F(x, y, z). The final version of the disparity vector V is outputted as the global motion vector.

In first step of the pyramidal implementation of the Lucas-Kanade algorithm, as shown at 201 and described above, a 3D-pyramid of the received 3D medical image A is built. In order to identify the global motion vector, V, A, and B should be defined according to a common coordinate system. However, as the coordinate systems of B and A may not match, B is sampled according to the coordinate system of A. Such sampling is performed in the following step, as shown at 202. During step 202, an initial motion vector is calculated on H that is defined as follows:

$$H = \left\{ \left( v_x + x \cdot \frac{hx'}{hx}, v_y + y \cdot \frac{hy'}{hy}, v_z + z \cdot \frac{hz'}{hz} \right) \right\}$$

During the following steps, as shown at 203-205, V is recursively refined over finer and finer grids until the final V is found. During the performance of the Lucas-Kanade algorithm in each one of the iterations, a different grid and a new V is used. As shown at 206, after the highest layer of the pyramid has processed by the Lucas-Kanade algorithm, the final V is outputted.

Figure 5:
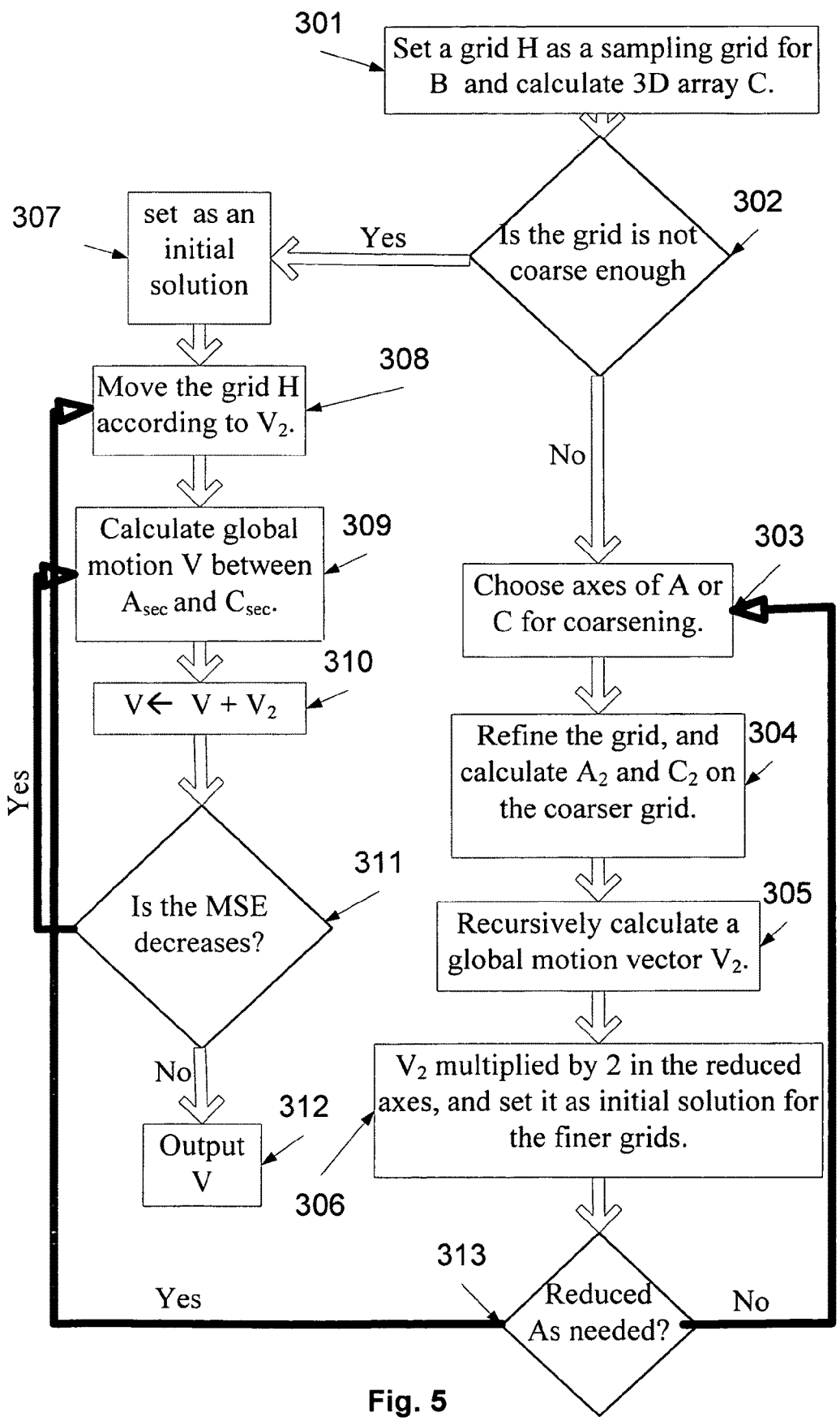
FIG. 5 is a flowchart of a recursive pyramidal implementation of the Lucas-Kanade algorithm, according to one preferred embodiment of the present invention.

Reference is now made to FIG. 5, which is a flowchart of a recursive implementation of the pyramidal implementation of the Lucas-Kanade algorithm, according to one preferred embodiment of the present invention. As depicted in steps 203-206 of FIG. 4, the pyramidal implementation of the Lucas-Kanade algorithm can be implemented recursively. FIG. 5 depicts such an implementation in a more detailed manner.

During the first step, as shown at 301, in order to sample the B in the resolution of A, C, a 3D array is calculated by taking H as a sampling grid for B with intervals of $$\left( \frac{hx'}{hx}, \frac{hy'}{hy}, \frac{hz'}{hz} \right).$$

The initial H is an outcome of aligning one corner of A with a respective corner of B. It should be noted that if recursive calls are used, the coordinate system does match, and therefore this step is redundant and therefore ignored.

During the following steps, as described above, H is coarsened to the required level. As shown at 302, if the grid H is not coarsened as required a coarsening sub-process is initiated. The coarsening sub-process continues until the size of H is adjusted. Preferably, as shown at 313, the recursive coarsening ends when the length of one of the axes of the grid decreases below a predefined threshold, preferably 16.

During the first step of the coarsening sub-process, as shown at 303, axes of A or C are chosen for coarsening. In order to promise that the intervals [hx', hy', hz'] are not substantially different one from the other, axes are chosen with minimal size for coarsening. For example, if hz' is twice as large as hx' and hy', a more isotropic grid with [2hx', 2hy', hz'] is produced.

During the following step, as shown at 304, one or more of the axes of A or B are reduced. When axis in A is reduced, we take an average value of every two consecutive voxels in the reduced axis. When axis in B is reduced, the reduction is made over the grid of H.

Then, as shown at 305, a temporary global motion vector $V_2$ is calculated recursively on the reduced grids. In the following step, as shown at 306, $V_2$ is multiplied by 2 in all dimensions in which the grid has been reduced in order to match with the global motion on the finer grid. $V_2$ can now be used as an initial solution for refinement.

In such a manner, the grid is iteratively reduced to the required level. As shown at 313, if the coarsening sub-process, which is depicted in steps 303-306, has been finished and the grid has been adequately reduced, the initial solution is [0,0,0] and the H grid is updated according to $V_2$, as shown at 308. Such an update promises that the coordinate systems of H and A are correlated.

For clarity, C denotes a re-sampled version of B according to the displacement of H according to $V_2$. However, the coordinate systems of A and C may be coordinated, as described above, A and C may still depicts different images of a common 3D space. Therefore, A and C should be reduced to cover only in the points that exist in both grids. For clarity, $A_{sec}$ and $C_{sec}$ denote 3D arrays that represent the intersection of A and C.

Now, after $A_{sec}$ and $C_{sec}$ are correlated and depicted the same 3D space, the global motion V can be calculated, as shown at 309, according to a global-motion algorithm. F and G denote a smoothened version of $A_{sec}$ and $C_{sec}$ respectively. F and G are preferably smoothed by a 3D Gaussian filter having a kernel with σ=1. $f_x$ denotes a numerical derivative of G in a first axis, $f_y$ denotes a numerical derivative of G in a second axis, $f_t$ denotes a 3D array that equal to G−F, and $f_z$ denotes a numerical derivative of G in a third axis.

The numerical derivative is calculated using a linear filter on the relevant axis. Preferably, the filter $$\left[ +\frac{1}{12}, -\frac{2}{3}, 0, +\frac{2}{3}, -\frac{1}{12} \right]$$

is applied. Then, an element wise multiplication is performed by multiplying each member of the group $F_i = \{f_x, f_y, f_z, f_t\}$ with all the members of Fi, in a manner that allows the calculation of $f_x^2$, $f_x f_y$, $f_x f_z$, $f_x f_t$, $f_y^2$, $f_y f_z$, $f_y f_t$, $f_z^2$ and $f_z f_t$. All the multiplications are summed over the grid. Then, the global-motion vector $V=[u, v, w]$ is calculated according to the following linear system of equations:

$$\begin{bmatrix} \sum f_x^2 & \sum f_x f_y & \sum f_x f_z \\ \sum f_x f_y & \sum f_y^2 & \sum f_y f_z \\ \sum f_x f_z & \sum f_y f_z & \sum f_z^2 \end{bmatrix} \cdot \begin{bmatrix} u \\ v \\ w \end{bmatrix} = \begin{bmatrix} \sum f_x f_t \\ \sum f_y f_t \\ \sum f_z f_t \end{bmatrix}$$

In another embodiment of the present invention, the global-motion vector $V=[v_x, v_y, v_z]$ is calculated in a structure tensor approach. In such an approach $A_{sec}$ and $C_{sec}$, which are respectively marked with F and G, are not smoothened. The multiplications of $F_i$ are calculated as described above. In the structure tensor approach the multiplications, $f_x^2$, $f_x f_y$, $f_x f_z$, $f_x f_t$, $f_y^2$, $f_y f_z$, $f_y f_t$, $f_z^2$ and $f_z f_t$ are smoothed using a 3D Gaussian filter.

The smoothed multiplications are used to construct the structure tensor. When the structure tensor approach is applied, V is calculated according to the following linear system of equations:

$$\begin{bmatrix} \sum K*f_x^2 & \sum K*f_x f_y & \sum K*f_x f_z \\ \sum K*f_x f_y & \sum K*f_y^2 & \sum K*f_y f_z \\ \sum K*f_x f_z & \sum K*f_y f_z & \sum K*f_z^2 \end{bmatrix} \cdot \begin{bmatrix} u \\ v \\ w \end{bmatrix} = \begin{bmatrix} \sum K*f_x f_t \\ \sum K*f_y f_t \\ \sum K*f_z f_t \end{bmatrix}$$

where K denotes a smoothening filter that is preferably a filter with a Gaussian kernel K.

In the following step, as shown at 310, V is used as a fine-tuning global motion vector which is added to a previously calculated $V=V+V_2$. Clearly, if V is calculated in the first iteration of the global motion calculation, then $V=V_2$.

As shown at 311, the fine-tuning calculation of the global motion vector V is repeated as long as the MSE of the adjustment $$MSE = \frac{1}{|A_{sec}|} \sum (A_{sec} - C_{sec})^2$$

gets smaller. Each time the process is repeated, the new V is labeled as the previous V. As shown at 312, when the MSE stabilizes on a certain value, the calculated V is outputted as the global motion vector.

Preferably, the 3D Gaussian filter K convolved on the 3D arrays F and G. In order to avoid boundaries problems during the convolution, the 3D Gaussian filter K is applied with a normalized Gaussian kernel K. Preferably, the convolution is carried out on G, F and on an additional 3D array that is filled with ones and has the same size as G and F. Afterwards, we normalized the elements of G and F by the dividing each element with a corresponding element of the convoluted version of the additional 3D array.

Reference is now made, once again, to FIG. 3. The first sub-module 401, as described above, has calculated the global motion vector according to the reference and source images. Now, the global motion vector, the reference record, and the source image are forwarded to the 3D affine transformation sub-module 402. The projection of the global motion vector on the reference image allows the generation of the shifted reference image, as described above.

As described above, the reference record preferably comprises a list of marker points, which may be used as distinctive features. The 3D affine transformation sub-module 402 is designed to generate an affine transformation matrix that is based on the differences between the positioning of respective descriptors in the source image and the shifted reference image. The affine transformation sub-module 402 is designed to extract a list of marker key-points and their descriptors, both from the source image and the shifted reference image. The list of distinctive features is preferably invariant to image 3D scale, 3D rotation, and partially invariant to changing in 3D viewpoints. The list of descriptors that is extracted from the source image is then matched with a respective list of reference descriptors that is associated with the reference image.

The respective list is preferably generated in advance and stored in the reference record that comprises the related reference image. In such a manner, the list of reference descriptors that is associated with the reference image has to be calculated only once. After the list of descriptors has been generated from the source image, it is matched with the stored list of reference descriptors. Based on the match, an affine transformation matrix is found, that allows the generation of the aforementioned transformed and shifted reference image.

Figure 6:
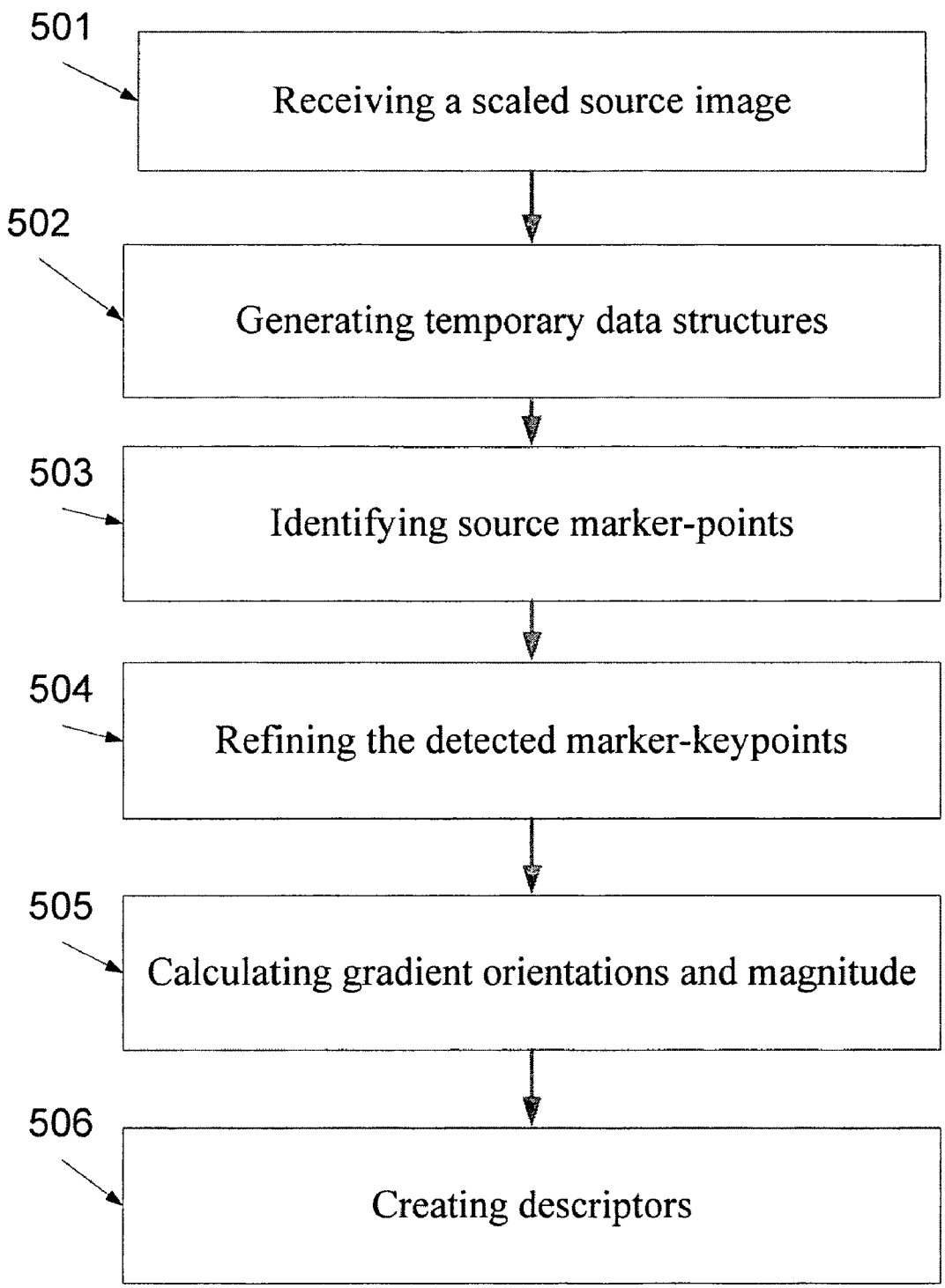
FIG. 6 is a flowchart of a five steps method that is implemented by an affine transformation sub-module, according to a preferred embodiment of present invention.

Reference in now made to FIG. 6, which is a flowchart of a five steps method, which is implemented by the 3D affine transformation sub-module, for creating a list of descriptors, according to a preferred embodiment of present invention. During the 3D affine transformation process, which is performed by the 3D affine transformation sub-module, a list of descriptors is generated according to the method depicted in FIG. 6. The figure presents a method for extracting descriptors, which are distinctive invariant 3D features, from the source image. The same method may also be used for extracting, in advance, distinctive invariant 3D features from the reference image, as described above.

During the first step, as shown at 501, the source image is received. Then, as shown at 502, the source image is used to generate temporary data structures, such as 3D difference of Gaussians (DoGs).

The process for building the DoGs includes a number of steps. First, the source image is iteratively smoothed six times by a set of six 3D Gaussian filters, where the filters diverse in their size. Such a set is preferably called a sextuplet.

After the first sextuplet is generated, each Gaussian image is down-sampled, preferably by a factor of 2. Preferably, this process is repeated, for creating more sextuplets. The process of down sampling is repeated until one of the image dimensions is smaller that 16 pixels. For example, if the source image size is 512×512×200, the down sampling is repeated four times. Let us denote the number of down sampling as NumOfDownSamp.

Finally, adjacent Gaussian 3D images of each sextuplet are subtracted to produce a set of five difference-of-Gaussian (DoG) 3D images. Totally, we end up with two structures: NumOfDownSamp sextuplets of Gaussians and NumOfDownSamp quintets of DoGs.

During the following step, the local extrema voxels, which may be referred to as the source marker-points, are detected from the DoGs, marker-points.

During the following section the process of finding a marker-point is described when a certain voxel X is evaluated as a local 3D extrema, wherein such a voxel is detected as a marker-point. A voxel is identified as a local exterema, if it is defined as the maxima. In order to evaluate whether it is the maxima or not the voxel is compared with 80 other voxels. The 80 other voxels comprises 26 immediate neighboring voxels, which are preferably located in a 9×9×9 voxels' cube at the current 3D DoG image and 54 voxels, which are preferably located at the respective two 9×9×9 voxels' cubes at the adjacent 3D DoG images, in the same quintets. The candidate voxel X is selected as a local extrema only if it is larger or smaller than all the 80 compared neighboring voxels.

In order to reduce the computational complexity of this step, only voxels from predefined areas are probed. As described above, on subsequent steps the chosen marker-points are used for the generation of a list of source descriptors that is matched with a respective list of reference descriptors that is related to the reference record. As further described above, each reference record comprises a segmented image in which areas the depicted organ are tagged. Such a segmented image can be used to identify in which areas relevant descriptors may be found. In order to reduce the computational complexity, only voxels of the source image, which are in areas that match areas in which reference descriptors can be found, are processed in the affine transformation process.

At the end of step 503, a set of marker-keypoints is generated.

During the following step, as shown at 504, the set of chosen marker-keypoints is refined. Preferably, during the refinement process, chosen marker-points, which are below or above one or more thresholds, are extracted from the set. For example, marker-points with low contrast or with characteristics of an edge are extracted from the set. In addition, the refinement of the marker point location creates a sub-pixel location. For example, after location refinement of a certain voxel, that may be referred to as [x, y, z], the marker point is located at [105.1, 55.4, 23.8] instead of [105, 55, 24].

During the fourth step, as shown at 505, 3D gradient orientations and gradient magnitude are calculated and assigned to each one of the chosen marker-points that have not been removed in previous steps. The calculation and assignment are preferably performed on local image gradient directions.

As the calculation is performed in the 3D domain, the gradient orientation is represented in spherical coordinates, using horizontal and vertical angles. Each one of the marker-points is assigned with an orientation that is the most common orientation among the neighboring 3D voxels. If there are multiple dominant orientations, the probed marker-points are assigned to these multiple orientations During the fifth step, as shown at 506, the generation of the descriptors is done. For each one of the remained marker-points, a descriptor is created. The descriptor is preferably represented by an array. The descriptor of each one of the marker-points is calculated by computing the gradient magnitude and orientation of the neighboring voxels in a region around the local extrema voxel. Preferably, the region is a cube of 8×8×8 voxels that is chosen relatively to the orientation of the probed marker-point.

Then, the region is divided into four sub-regions. Preferably, each sub-region is a cube of 4×4×4 voxels. For each one of the sub-regions, orientation histograms are accumulated and divided into 8 bins. For example, if the range of an orientation histogram is between 0° and 360°, each bin sequentially covers a section of 45°.

After the sub-regions orientation histograms are accumulated and divided, the descriptor is created. The descriptor comprises eight bins, wherein each one of the bins represents the orientation distribution in a related sub-region. Preferably, each descriptor separately represents eight sub-regions. Each sub-region is represented by a vertical and horizontal orientation distributions sub-records. As each sub-record requires 8 bytes, the total size of such a preferred descriptor is 128 bytes: ((8+8)·8). Each descriptor is assigned to each marker-point. Each arrangement of a descriptor and respective marker point is preferably tagged as a distinctive feature. The outcome of this step is preferably a list of distinctive features.

As further described below, the descriptors are used for matching between different views of the same feature in the source image and the scaled reference image. The features are invariant to scale, rotation, affine distortion, changes in 3D viewpoint, and to noise.

At this time, as the list of distinctive features of the source image is calculated and the respective list of distinctive features that has been received with the reference record is available, as described above, an affine transformation matrix can be evaluated.

The matrix evaluation process may be divided in to two steps. During the first step, a match between a set of source feature points and a set of reference feature points. During the second step, the affine matrix is evaluated, based on the match.

During the matching process, which is based on statistical considerations, an initial outliers filtering is performed. The filtering derives a set of inliers which statistically reinforces the uniformity of the transformation. These inliers can be found by using commonly known algorithms, such as the k-nearest neighbor matching algorithm, random sample consensus (RANSAC) algorithm, Hough transform, etc.

In order to improve the inliers estimation and to avoid inaccurate matching that is based on inaccurate symmetry calculation, a preliminary splitting of the head is performed. Preferably, the splitting is performed after the ellipsoids in the reference image to the ellipsoids in the source image are fitted. Such a splitting a may be used for rejecting an inaccurate match between a certain side in the reference image and an opposite side in the source image. Such a fitting is performed by minimizing the ellipsoid function to the wire frame of the 3D images. The wire frame of an image may be obtained by standard edge detection between the brain and the surrounding thereof.

Therefore, at this point we have a set of inliers (couples of source-reference feature). The extraction of the affine transformation array is a 4×4 matrix that can be represented as follows:

$$\begin{bmatrix} m1 & m2 & m3 & t1 \\ m4 & m5 & m6 & t2 \\ m7 & m8 & m9 & t3 \\ 0 & 0 & 0 & 1 \end{bmatrix}$$

where t1-t3 represent linear transformation between a source descriptor in the source image and a respective reference descriptor that is related to the reference record, m1-m9 represent affine transformation between the inliers source descriptors to the respective inliers reference descriptors. The affine transformation matrix, the source descriptor and the reference descriptor can be represented as follows:

$$\begin{bmatrix} u \\ v \\ w \\ 1 \end{bmatrix} = \begin{bmatrix} m1 & m2 & m3 & t1 \\ m4 & m5 & m6 & t2 \\ m7 & m8 & m9 & t3 \\ 0 & 0 & 0 & 1 \end{bmatrix} * \begin{bmatrix} x \\ y \\ z \\ 1 \end{bmatrix}$$

Where [u, v, w, 1] denotes the values of a source descriptor and [x, y, z, 1] denotes the values of a reference descriptor. For a single match, the last equation can be written as follows:

$$\underbrace{\begin{bmatrix} x & y & z & 0 & 0 & 0 & 0 & 0 & 0 & 1 & 0 & 0 \\ 0 & 0 & 0 & x & y & z & 0 & 0 & 0 & 0 & 1 & 0 \\ 0 & 0 & 0 & 0 & 0 & 0 & x & y & z & 0 & 0 & 1 \\ \cdots & \cdots & \cdots & \cdots & \cdots & \cdots & \cdots & \cdots & \cdots & \cdots & \cdots & \cdots \\ \cdots & \cdots & \cdots & \cdots & \cdots & \cdots & \cdots & \cdots & \cdots & \cdots & \cdots & \cdots \end{bmatrix}}_{A\text{-reference descriptors}} * \underbrace{\begin{bmatrix} m1 \\ m2 \\ m3 \\ m4 \\ m5 \\ m6 \\ m7 \\ m8 \\ m9 \\ t1 \\ t2 \\ t3 \end{bmatrix}}_{x\text{-the transformation}} = \underbrace{\begin{bmatrix} u \\ v \\ w \\ \vdots \end{bmatrix}}_{B\text{-source descriptors}}.$$

Each one of the found inliers is substituted in the above equation, creating a multiple linear equations problem of the form Ax=B. Solving this problem and extracting x is, again, a well known problem that can be solved using the pseudo-inverse solution, x=$[A^T A]^{-1} A^T b$.

Reference is now made, once again, to FIG. 3. As depicted in FIG. 3, the outputs of the 3D affine transformation sub-module 402 are forwarded to the optic-flow sub-module 403 which is used to generate an optic-flow structure based thereupon. The optic-flow sub-module 403 receives the reference record, the source image, and the affine transformation array that has been calculated by the 3D affine transformation sub-module 402 and generates based thereupon an optic-flow field that can be used to match each voxel in the source image to a respective voxel in the transformed and shifted reference image. The optical flow field is a vector field that shows the direction and magnitude of the intensity changes of each voxel from the source image to the transformed and shifted reference image.

Reference is now made to FIGS. 9A and 9B, which are flowcharts of an iterative process for calculating an optic-flow field, according to one preferred embodiment of the present invention. The affine transformation vector that is calculated during the 3D affine transformation process may be used to acquire an optic-flow field between the transformed and shifted reference image and the source image.

The optic-flow algorithm is a 3D implementation of the optic-flow algorithm that has been published by A. Bruhn et al., see A. Bruhn et al. *Real-Time Optic-flow Computation with Variational Methods*. In N. Petkov, M A. Westenberg (Eds.): *Computer Analysis of Images and Patterns. Lecture Notes in Computer Science*, Vol. 2756, Springer, Berlin, 222-229, 2003 and A. Bruhn et al., "*Combining the advantages of Local and Global Optic-flow Methods*, L. Van Gool (Ed.), *Pattern Recognition, Lecture Notes in Computer Science*, Vol. 2449, Springer, Berlin, 454-462, 2002 (hereinafter: "the Bruhn algorithm"), which are incorporated in their entirety by reference into the specification.

For clarity, the following notations are used in this section:
$F_1(\vec{x})$—The reference image
$F_2(\vec{x})$—The source image $\vec{g} = [u(\vec{x}), v(\vec{x}), w(\vec{x})]^T$—A motion field $\vec{g}: \Re^3 \alpha \Re^3$
$F_3(\vec{x})$—The reference image $F_1(\vec{x})$ translated by $\vec{g}$ The optic-flow module generates a motion field between $F_1$ and $F_2$. $F_3$ and $F_2$ should be consistent, preferably similar, as measured by a constancy term, and the motion field should be smooth according to a smoothness term. Those terms are measured by an energy function, which is minimized by the optic flow motion field.

As shown at 701, during the first step, an initial motion field is set according to the 3D affine transformation registration. During the following steps, as shown at 702 and 703, an iterative process is used for finding the optic-flow field. During each one of the iterations, a ($\vec{g}_i(\vec{x})$) is identified and added to the final optic-flow field, denoted by $\vec{g}(\vec{x})$. The calculation of each $\vec{g}_i(\vec{x})$ is based on previously calculated $\vec{g}(\vec{x})$. Preferably, during the first iteration $\vec{g}(\vec{x})$ is utilized with the values of the affine transformation array. The iterative process lasts a predefined number of iterations, sufficient for convergence of the optic-flow motion field.

Figure 7:
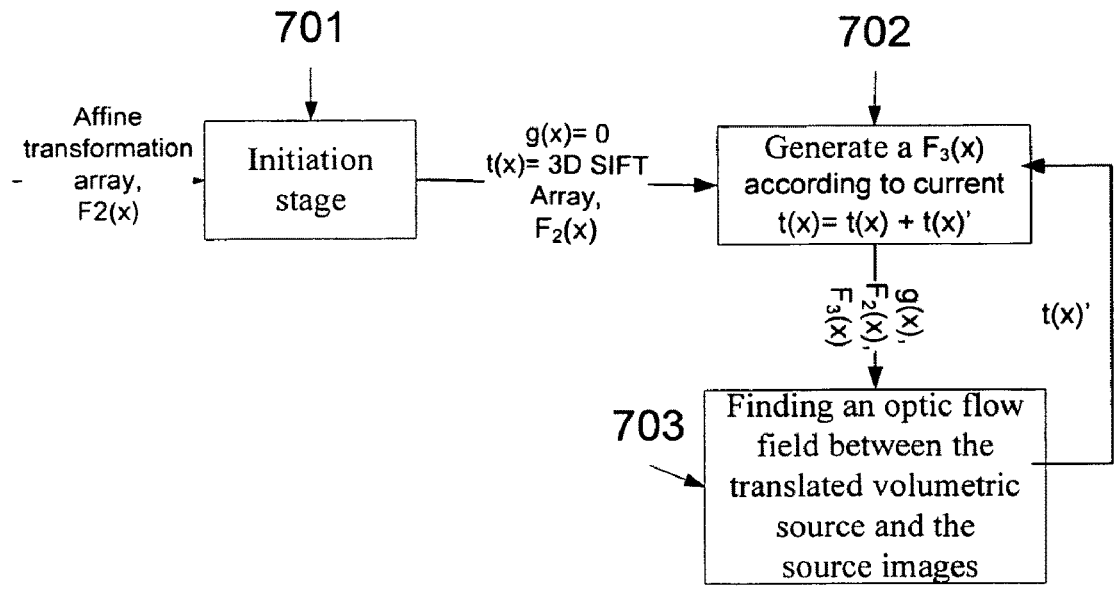
FIG. 7 is a flowchart of an optic-flow algorithm, which is performed by the registration module, according to a preferred embodiment of present invention.
Figure 8:
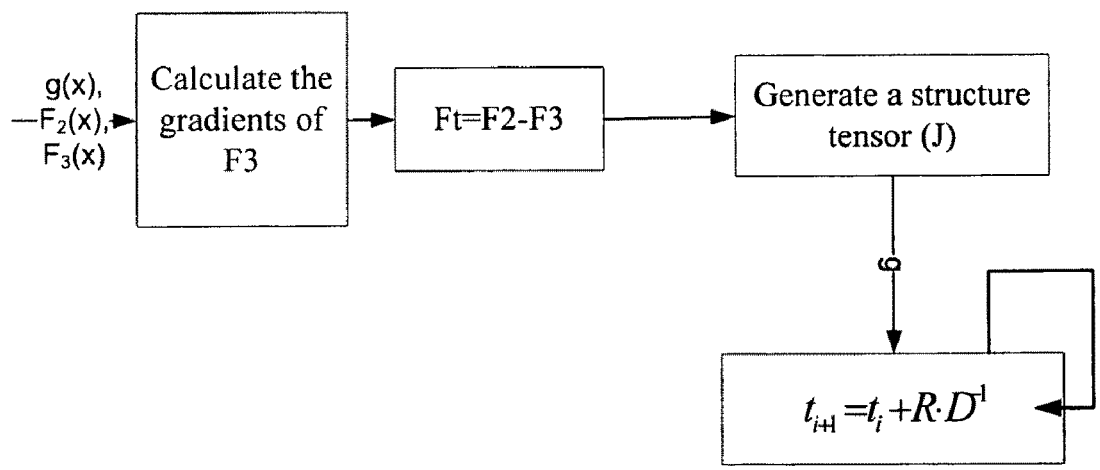
FIG. 8 is a flowchart of an optic-flow sub-process that is performed during step 703 of FIG. 7, according to one preferred embodiment of the present invention.

Reference is now made to FIG. 8, which is a flowchart of the optic-flow process that is performed during step 703 of FIG. 7, according to one embodiment of the present invention. As described above, during each one of the iterations of the iterative process, which is depicted in FIG. 7, $\vec{g}_i(\vec{x})$ is calculated and $\vec{g}_i(\vec{x})$ added to $\vec{g}(\vec{x})$, where $\vec{g}_i(\vec{x})$ is preferably calculated using a variant of the aforementioned Bruhn algorithm.

With the 3D Bruhn algorithm, the energy function is $$E = \int \left( \begin{bmatrix} u \\ v \\ w \\ 1 \end{bmatrix}^T \cdot K_\sigma * \begin{bmatrix} f_x^2 & f_x f_y & f_x f_z & f_x f_t \\ f_x f_y & f_y^2 & f_y f_z & f_y f_y \\ f_x f_z & f_y f_z & f_z^2 & f_z f_t \\ f_x f_t & f_y f_t & f_z f_t & f_t^2 \end{bmatrix} \cdot \begin{bmatrix} u \\ v \\ w \\ 1 \end{bmatrix} + \alpha(|\nabla u|^2 + |\nabla v|^2 + |\nabla w|^2) \right) d\vec{x}$$

where $f_x$, $f_y$, and $f_z$ are the derivatives of $F_1$, sampled at the points of $\vec{g}(\vec{x})$, and $f_t = F_3 - F_2$. $K_\sigma$ is a Gaussian kernel with standard deviation σ, which convolutes each element of the matrix separately. J is the structure tensor $$J = K_\rho * \begin{bmatrix} f_x^2 & f_x f_y & f_x f_z & f_x f_t \\ f_x f_y & f_y^2 & f_y f_z & f_y f_t \\ f_x f_z & f_y f_z & f_z^2 & f_z f_t \\ f_x f_t & f_y f_t & f_z f_t & f_t^2 \end{bmatrix}$$

In order to calculate the temporary motion field $\vec{g}_t(\vec{p})=[u_t(\vec{p}),v_t(\vec{p}),w_t(\vec{p})]^T$ which minimized the energy function, the following a set of Euler-Lagrange equations has to be solve:

$$\begin{cases} \Delta(u+u_t) - \frac{1}{\alpha}(J_{11}u_t + J_{12}v_t + J_{13}w_t + J_{14}) = 0 \\ \Delta(v+v_t) - \frac{1}{\alpha}(J_{21}u_t + J_{22}v_t + J_{23}w_t + J_{24}) = 0 \\ \Delta(w+w_t) - \frac{1}{\alpha}(J_{31}u_t + J_{32}v_t + J_{33}w_t + J_{34}) = 0 \end{cases}$$

where $\Delta$ is a 3D Laplacian operator.

The solution, $\vec{g}_t$, can be found using various relaxation methods, including Gauss-Seidel red-black relaxation or dumped Jacobi relaxation.

For acceleration of the convergence speed, standard multi-grid methods can be used, where affine transformation based motion field is calculated recursively for the coarsest grid to the finest one.

Applying the optic-flow field on the transformed and shifted reference image allows the generating of a registered reference image, as described above. The registered reference image has been generated by transforming each voxel in the transformed and shifted reference image according to the location of a respective voxel in the source image, as described above.

Reference is now made, once again, to FIG. 3. As described above, the optic sub-module 403 outputs the optic-flow field. The optic-flow field, together with the transformed and shifted reference image and the source image are the outputs of the registration module 101.

Reference is now made, once again, to FIG. 2. As depict in FIG. 2, the registration module is connected to a segmentation module 102. The segmentation module 102 is designed to receive the source image, the reference record, and the optic-flow field from the registration module 101. As described above, each reference record comprises a segmented image that is a tagged version of the reference image. In the segmented image, different areas of the depicted organ are tagged with different values. Such segmentation allows the segmentation module 102 to respectively segment areas of the organ that is depicted in the received source image.

For clarity, S denotes the segmented image, and $S_c$ denotes a specific area in S.

Preferably, the actual segmentation process of $S_c$ comprises few steps. During the first step, as described above, all the voxels of $S_c$ are labeled with a tag, which is, for clarity, denoted by c. All the other voxels are labeled with another tag, such as 0.

The optic-flow motion field, which is denoted by the variables [U, V, W], is used to find the tagged segments in the source image. The tagged segments are preferably identified by implementing the following equation:

$$T_c(x, y, z) = S_c\left(x \cdot \frac{hx'}{hx} + U(x, y, z), y \cdot \frac{hy'}{hy} + V(x, y, z), z \cdot \frac{hz'}{hz} + W(x, y, z)\right)$$

Where $T_c$ denotes a one-label segmentation map of $S_c$. $T_c$ is calculated using a standard tri-linear interpolation of $S_c$. As an interpolation technique is used, voxels of the $T_c$ array that match voxels of the received source image are tagged with the value 1 while others are tagged with the value 0. Preferably, voxels of the $T_c$ array that match voxels identified as the boundaries of the area $S_c$ are tagged with a real number between 0 and 1. The real number of a certain voxel can be regarded as a probability measure, expressed as percentage, for the relevancy of the voxel to the area tagged in $T_c$.

$T_c$, which may be referred to as a reference segment or a segmentation map, is now a one-label segmented image of the received source image in which one area of the organ that is depicted in the source image. The respective area in the source image may be referred to as a source segment. This process is repeated for a number of areas in the source image until all the areas in the segmented image have identified and tagged in the source image. For example, if the organ that is depicted in the received source image is the brain, a segmentation map can be generated for a number of brain areas such as the cerebellum, white and gray matter, the ventricular system as a whole, or separate parts of it, such as the lateral ventricles, the third and the fourth ventricles, and the frontal and temporal horns, various cisterns, such as the cisterna magna, the ambient cistern, the suprasellar cistern, the prepontine cistern, the caudate nucleus, the thalamus nucleus, the corpus-callosum, the bone as a whole and its various parts, such as the frontal bone, the parietal bone, the temporal bone, the various sutures, such as the coronal suture, sagittal suture, and lambdoid suture, the sagittal sinus, and the brain as a whole.

Reference is now made, once again, to FIG. 2. The segmentation module 102 is designed to generate a segmentation structure, such as an array of reference segments, which allows the segmentation of the source image. The source image, the optic field, and the segmentation structure are forwarded to the feature extraction module 103, preferably via an active contour (AC) 107 sub-module. The location information, which is stored in the segmentation structure, is used in the feature extraction process that is performed by the feature extraction module 103. The location information indicates which voxels of the source image depicts a certain anatomical structure, an organ, or a certain area. The segmentation structure comprises a number of reference segments, each associated with a certain anatomical structure, an organ, or a certain area. The AC sub-module is designed to enhance and refine the reference segments according to the source image using the prior knowledge of shape and color of each such segment. If the source image is 3D CT image, the enhancement and refinement are preferably performed by separately applying a level-set evolution process with a unique Hounsfield unit (HU) based adaptive procedure, and the use of shape prior, on each one of the reference segments of the segmentation structure. The general guidelines of AC procedure are described a number of published articles and books, such as S. Osher, N. Paragios, geometric level set methods in imaging, vision, and graphics, Springer, 2003 and J. A. Sethian, level set methods and fast marching methods, Cambridge university press, 1999, which are herein incorporated in their entirety by reference into the specification.

Preferably, the basic AC methods are configured according to HU and shape based prior, which are used as additional terms within the minimized functional. It should be noted that various methods can be applied for the functional of shape based prior, see O. Faugeras, Statistical Shape Influence in Geodesic Active Contours, IJCV 2002, and N. Paragios et al, shape prior for level set representations, ECCV 2002, which is herein incorporated in its entirety by reference into the specification.

As for the HU based functional, for every segment, we have used a probability density function (PDF) based force term within the functional that is proportional to the expected HU within that segment.

In order to reduce the computational complexity of the level-set evolution process, each reference segment is assigned with a list of HU values of the respective anatomical structure, based on internal library of segmented references.

For clarify, the following notations are defined. I denotes the source image, u denotes a level set of a certain anatomical structure which is associated with a certain reference segment, g denote a positive edge indicator function, and PDF denotes the outcome of a PDF of HUs inside the source segment that matches the list of known HU expected to be found within that source segment which is preferably attached to the respective reference segment.

During the level-set evolution process, prior knowledge about the HU PDF of each reference segment and its shape are assimilated into the active contours scheme so that the evolution of the contour is motivated also by those adaptive local forces, which corresponds to the PDF and the shape, as explained earlier. This PDF force is the linear combination of forces, derived from the HU expected to be present within each anatomical structure.

In particular, the following evolution equation is used:

$$\frac{\partial u}{\partial t} = \alpha \cdot AC + \beta \cdot BF + \gamma \cdot AR + \delta \cdot HF + \lambda \cdot SF$$

where AC denotes the active contour functional, which can be implemented in different ways. For example, the active contour functional may be a geometric active contour, which is preferably defined as follows:

$$AC = a(x)|\nabla u|\text{div}\left(\frac{b(x)}{|\nabla u|}\nabla u\right).$$

BF denotes a balloon force term, causing the contour to shrink. It should be noted that BF can be implemented in many ways, for example as follows: $BF=g(x)\cdot|\nabla u|$. AR denotes a robust alignment variable, which is defined to align the contour to be perpendicular to the image gradient. There are a number of possible implementations, for example as follows: $AR=\text{sign}(<\nabla u, \nabla I>)\Delta I|\nabla u|$. HF denotes a HU based force variable, which is define to bring the contour to include voxels within a certain HU range, and to reject voxels with other HU. There are a number of possible implementations, for example as follows: $HF=P(I|PDF)|\nabla u|$. SF denotes the shape based force, which is defined to adjust the contour according to the model contour. There are a number of possible implementations, for example as follows: $SF=|\nabla u|\cdot s\cdot d\cdot \nabla d$, where d denotes the distance between the model contour UM and the current contour after transformation with scaling s, for example as follows: $d=d(u_M(x, y, z), u(A(x, y, z)))$ Reference is now made to FIG. 9, which is a flowchart of the level-set evolution process that is implemented by the AC sub-module for each one of the reference segments, according to a preferred embodiment of present invention.

During the first step of the level-set evolution process, as shown at 801, a distancing process is implemented on one of the source segments. Based on an initial level-set, a grid point of the reference segment, which is adjacent to the zero level set, is identified. Based thereupon the grid points of the reference segment are assigned with values corresponding with distances to the points of the initial level sets. The grid points of the reference segment, along with their values, are used in a fast marching method (FMM) scheme that is implemented with a narrow band and a multi-grid. The result is then multiplied with a sign function of the initial level set.

During the following step, as shown at 802, the convergence of the reference segment is evaluated according to a respective source segment. If the reference segment is converged, the process is terminated and u is outputted as the level-set. If not, u is recalculated, as described below.

At step 804, a balloon force (BF) is calculated, according to g(x), for the u of the anatomical structure that is represented in the segment. During the following step, as shown at 805, HUs based force (HF) is calculated.

During this process, for each HU value of the source segment, which is associated with a respective HU value in the list of HUs of the reference segment, a local force based on the PDF of that HU is calculated. For each voxel in the source segment, a probability p is calculated, where p denotes PDF (x) and x denotes the intensity level of the voxel. Accordingly, p is proportional to the local force at that voxel in the source segment. The local forces are summed to HF.

The, as shown at 812, the shape based force, which is defined to adjust the contour according to the model contour is calculated. During the following step, as shown at 806, a robust alignment force is calculated.

Now, after BF, HF, and AR are calculated force is added to the level set u of the source segment, preferably as follows:

$$u=\alpha\cdot u+\beta\cdot BF+\gamma\cdot AR+\delta\cdot HF+\lambda\cdot SF$$

During the following steps, u is updated, preferably using an unconditionally stable, efficient numerical scheme, such as the additive operator splitting (AOS). For example, as shown at 808-810, tri-diagonals $v_1$, $v_2$, and $v_3$ are calculated for i=1, 2, and 3, as shown at 808. $v_1$, $v_2$ and $v_3$ are extracted from a matrix Ai, which is preferably a matrix that is built according to the following equation:

$$a_{ijl} = \begin{cases} a_i|\nabla u|_i^n \frac{2}{\left(\frac{|\nabla u|}{b}\right)_i^n + \left(\frac{|\nabla u|}{b}\right)_j^n}, & j \in N_l(i) \\ -a_i|\nabla u|_i^n \sum_{m \in N_l(i)} \frac{2}{\left(\frac{|\nabla u|}{b}\right)_i^n + \left(\frac{|\nabla u|}{b}\right)_j^n}, & j = i \\ 0, & \text{else} \end{cases}$$

As shown at 810, $v_i$ is calculated in each one of the iterations by solving the following equation:

$$(I-\tau\cdot i\cdot A_i(u^n))v_{il}^{n+1}=u^n$$

Preferably, the equation is solved by a tri-diagonal matrix algorithm (TDMA), which is also known as the Thomas algorithm. The TDMA is a simplified form of Gaussian elimination that can be used to solve tridiagonal systems of equations.

During the following step, as shown at 811, $u^{n+1}$ is updated according to the values of $v_1$, $v_2$ and $v_3$. The update is preferably performed as follows:

$$u^{n+1} = \frac{1}{3}(v_1^{n+1} + v_2^{n+1} + v_3^{n+1})$$

The calculated $u^{n+1}$ is now used for re-distance u of the reference segment, as described above and shown at 801.

Figure 9:
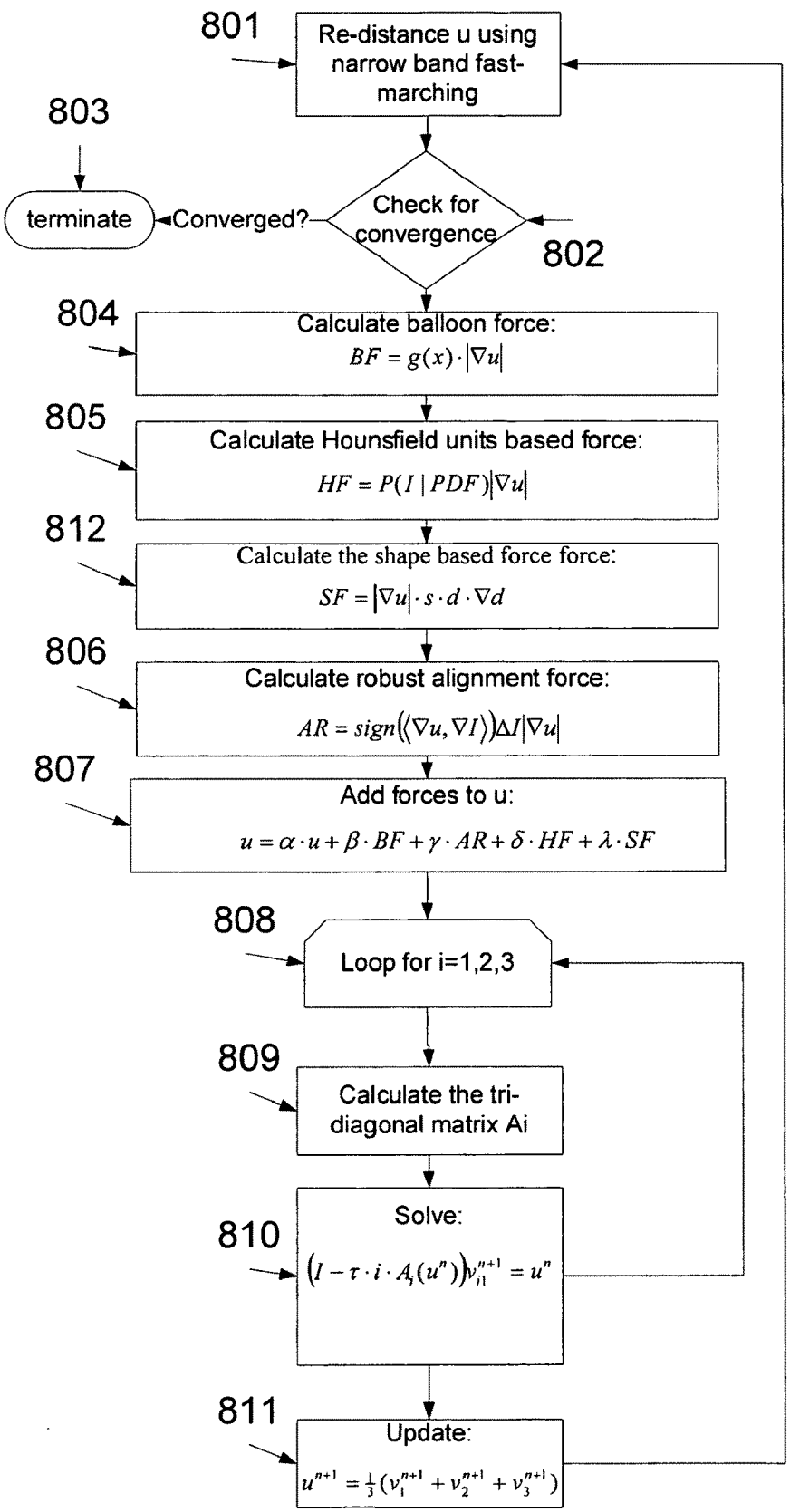
FIG. 9 is a flowchart of a level-set evolution process, according to a preferred embodiment of present invention.

Steps 801-811 in FIG. 9 describes an iterative process in which the level set of a certain reference segment is refined and enhances. The level-set evolution process is repeated for each one of the reference segments in the segmentation structure, thereby refine and enhance the results of the segmentation process that is described above. The output of the AC sub-module is a refined segmentation structure that comprises the enhanced reference segments.

Reference is now made, once again, to FIG. 2. As depicted, the feature extraction module 103 receives the refined segmentation structure from the AC sub-module 107, the optic-flow field from the registration module 101, and the source image, preferably from the segmentation module.

The Feature extraction module 103 is designed to generate a feature vector by applying various feature-extraction algorithms on the source image and on source segments thereof and grouping the output in the form of a vector. The feature vector is later used for estimating the priority level of the source image and for the detection of pathological indications in the organ that is depicted therein.

As commonly known, different pathologies can be identified by different indications that appear in the organ depicted in the source image. For example, the volume, the surface area, the moments, the general shape, the average color, the color standard deviation, and the contrast of colors of areas in the organ, the human body system, or a section thereof that is depicted in the source image can indicate on one or more pathologies.

As described above, the segmentation structure comprises location-based information that indicates which voxels of the source image depicts a certain organ or a certain area. The feature extraction module 103 uses the location information for implementing different estimation functions. The outcomes of the estimation functions are gathered and stored in a FV that is forwarded to the classification unit. The FV, as described above, may comprise medical and general information of the related patient. The values, which are stored in the feature vector, may later be used for prioritizing and classifying the source image according to different indications and for diagnosing pathologies of the organ that is depicted in the source image. Preferably, the medical information about the related patient that has been received with the source image is also stored in the FV.

As depicted in FIG. 2, the registration module 101 forwards the optic-flow field to the feature extraction module 103. As the feature extraction module 103 uses the optic-flow field with the segmentation maps of the segmentation structure for identifying the normality of areas in a certain organ. The optic-flow field can also be used, as described below, to identify deformations, asymmetry, local rotation moments, and optic-flow field discontinuities in one or more of the areas.

The estimation functions are based on a clinical-anatomical analysis that is adjusted according to the organ that is depicted in the source image. For example, if the source image is an image of different areas in the brain, the estimation functions may be used for evaluating different characteristics of different areas thereof. For example, the volume of the ventricles, the volume of the cerebrospinal fluid (CSF), the symmetry level between deferent structures within the brain, the position of the $3^{rd}$ ventricle with respect to the midsagittal plane (MSP), the presence of Hypodense and Hyperdense regions, and the completeness of the skull are estimated.

The evaluated features are used as diagnostic markers. Each one of the evaluated features may later be used for classifying the pathological level of the organ depicted in the source image or of areas thereof. The pathological levels may be used for alerting the system user that an abnormality has been identified in the source image or in areas thereof. It may also be used to split the pile of waiting cases for normal cases and ones that are suspicious as pathological.

As described above, the source image may comprise general background information about the patient to whom the organ belongs. Such information, as described above, may comprise personal information about the patient, such as his or her age, gender, and physical condition at the time the scan has been held. Preferably, an initial diagnosis is also included. The estimation functions also may be based on the general background information, as described below. The outputted feature vector may comprise this general background information and other medical information of the related patient. Such medical information may also be used as a diagnostic marker for the classification of the source image, as described below.

In one preferred embodiment of the present invention, the source and the reference images are four dimensional (4D) medical images of an organ, such as the heart. A 4D medical image is a data set composed of a time-series of 3D medical images that reflect the behavior of the depicted organ during a certain period. In such an embodiment, the reference and the source images may be correlated before they are being matched by the registration module 101. Matching a 4D medical image is important in organs such as the heart wherein the shape of the organ substantially change over time and can provide information about the pathological level thereof.

In the following section, a number of estimation functions are described. These estimation functions are exemplary and therefore other estimation functions may be used. Each one of the functions is based on the location information that is stored in the segmentation structure, the optic-flow field, and the source image.

A Volume Estimation Function

The volume estimation function is used for estimating the volume of a certain organ that is depicted in the source image or in a section thereof. The volume estimation function is based on the segment reference of the estimated organ or section and a sampling grid that is based on the source image and the optic-flow field.

As described above, $T_c$ denotes the segmentation map for the specific organ or a section thereof and [hx', hy', hz'] denote intervals of the sampling grid. The volume is calculated as follows:

$$V = hx' \cdot hy' \cdot hz' \cdot \Sigma T_c(x,y,z)$$

where the summation is done over x, y and z.

A Center-of-Mass Estimation Function

The center-of-mass estimation function is designed to estimate the center-of-mass of a certain area in the organ that is depicted in the source image or section thereof. The center-of-mass estimation function is based on the segmentation map of the estimated organ or section and on a sampling grid that is based on the received source image and the optic-flow field.

The center-of-mass is a first order moment of the segmentation map. As described above, $T_c$ denotes the segmentation map for the specific organ or a section thereof. G denotes the sampling grid.

(I, J, K) denote the dimensions of G, (X, Y, Z) denote the primal axes of G, [hx', hy', hz'] denotes the intervals of G. The origin of the sampling grid is defined as the center of G.

The center-of-mass of the specific organ or a section thereof, which are tagged in the segmentation map, is calculated as follows:

$$C_x = \Sigma x \cdot T_c(x,y,z)/\Sigma T_c(x,y,z)$$

$$C_y = \Sigma y \cdot T_c(x,y,z)/\Sigma T_c(x,y,z)$$

$$C_z = \Sigma z \cdot T_c(x,y,z)/\Sigma T_c(x,y,z)$$

A Primal Axes (PAs) Estimation Function

The PAs estimation function estimates second order moments of a certain organ, which is depicted in the source image, or an area thereof. The primal axes estimation function is based on one of the segmentation map on the segmentation structure and on a sampling grid that is based on the source image and the optic-flow field. The output of the PAs estimation function is a rotation matrix and scaling vector.

For clarity, V denotes the received segmentation map, G denotes a sampling grid, (I, J, K) denote the dimensions of the grid G, (X, Y, Z) denotes the primal axes of G, and [hx', hy', hz'] denote the intervals of G. The grid origin is defined at the center of G. The PAs estimation function uses the aforementioned center-of-mass estimation function to calculate ($C_x$, $C_y$, $C_z$) that denotes the center-of-mass of (x, y, z).

During the first step the PAs estimation function calculates the following matrix:

$$M = \begin{pmatrix} m_{200} & m_{110} & m_{101} \\ m_{110} & m_{020} & m_{011} \\ m_{101} & m_{011} & m_{002} \end{pmatrix}$$

where $$m_{pqr} = \frac{1}{\sum_{i=1}^{U}\sum_{j=1}^{V}\sum_{k=1}^{W} V[x,y,z]} \sum_{i=1}^{U}\sum_{j=1}^{V}\sum_{k=1}^{W} (x-C_x)^p \cdot (y-C_y)^q \cdot (z-C_z)^r$$

During the following step, a singular value decomposition (SVD) process is applied on the matrix M. The SVD process is generally well known and therefore it is not described here in greater detail. During the SVD process, the rotation matrix U is identified as $M = USU^T$, where S denotes a diagonal scaling matrix.

A Surface Area (SA) Estimation Function

The SA estimation function is designed to estimate the surface area of a certain organ, which is depicted in the source image, or an area thereof. The SA estimation is based on one of the segmentation maps of the segmentation structure and on a sampling grid that is based on the source image and the optic-flow field, as described below.

Preferably, the calculation of the surface is performed according to the marching cubes algorithm. The marching cubes algorithm creates a triangulation mesh of zero-crossing surface of a 3D function from the segmentation map and the sampling grid. The marching cubes algorithm is generally well known and therefore is not described here in greater detail.

The surface area of an organ or a section thereof can be calculated, inter alia, according to one of the following processes:

During the first step of the first surface area calculation, a marching cubes algorithm is applied on the segmented image of the source record of the organ. As described above, the marching cubes algorithm outcome is a mesh triangulation of the surface. The mesh triangulation comprises points (P) and triplets (TR) of the points that reflect the points' triangulation. Then, for each point (p) of P, a motion field is calculated using a tri-linear interpolation.

During the following step, all the points of P are shifted according to a related motion field that is an outcome of the tri-linear interpolation. The shift adjusts the mesh to the source image. Preferably, all the points of P are shifted according to the following:

$$p' \leftarrow p + [U(p), V(p), W(p)]$$

Where p' denotes the value of one of the P's points, after the motion field has been applied. P' denotes the shifted version of P.

Then, by measuring the triangulation of P' and TR, the surface of organ c in the source image is calculated.

During the first step of the second surface area calculation the marching cubes algorithm is applied on the segmentation map $T_c - 0.5$. As described above, the marching cubes algorithm outcome is a mesh triangulation of the surface. The mesh triangulation comprises points (P) and triplets (TR) of the points that reflect the points' triangulation. Then the triangulation of the surface area of the organ in the source image is calculated. For each triangle in the TR the surface area is calculated.

For clarity, $(t_1, t_2, t_3) \in TR$ denote the indexes of vertices of a certain triangle in the triangulation. $(t_1, t_2, t_3) \in TR$. During the triangulation the following substitution $p_1 = P(t_1)$, $p_1 = P(t_1)$ and $p_1 = P(t_1)$ is performed, where $P_1$, $P_2$, and $P_3$ denote the actual vertices.

During the next step, the points are normalized by multiplying their elements by the points of [hx', hy', hz'].

Then area of each one of the triangles is calculated by the following equation:

$$\text{Triangle} = \frac{1}{2}|v_1 \times v_2|$$

where $$v_1 = p_2 - p_1, \, v_2 = p_3 - p_1, \text{ and } \frac{1}{2}|v_1 \times v_2|$$

denotes the cross product between $v_1$ and $v_2$. The surface area is calculated by summing the area of all the triangles.

A Color Average/STD Estimation Function

The color average/STD estimation function is designed to estimate the average color of a certain organ that is depicted in the source image or an area thereof. The color average estimation function is based on the segmentation map of the estimated organ, the source image, and the optic-flow field.

The calculation of the average color of an organ or a section thereof, using the segmentation map of the organ, is a weighed mean color that is calculated as follows:

$$\text{color} = \frac{\sum T_c(x,y,z) \cdot A(x,y,z)}{\sum T_c(x,y,z)} = \frac{\sum T_c \cdot A}{\sum T_c}$$

The weighed standard deviation is calculated as follows:

$$std^2 = \frac{\sum T_c \cdot \sum T_c \cdot A^2 - \left(\sum T_c\right)^2 \cdot \left(\sum A\right)^2}{\left(\sum T_c\right)^2 - \sum T_c}$$

The output of this estimation function is the outcome of both calculations.

A Spherical Fourier Transform (SFT) Estimation Function

The Organ Shape's SFT estimation function is designed to find characteristics of the shape of a certain organ, which is depicted in the source image, or of a section thereof. The SFT estimation function is based on one of the segmentation maps of the segmentation structure and on a sampling grid that is based on the source image and on the optic-flow field. The output is a set of SFT coefficients that is preferably represented in an array.

The SFT spherical coefficients efficiently characterize a sphere function using spherical Fourier functions. The SFT spherical coefficients can be used to characterize the shape of the organ that is depicted in the source image or in a section thereof. Preferably, the SFT estimation function defines a spherical function that calculates the distance between the surface of the organ and the center-of-mass thereof. According to such a function, the spherical coefficients can be calculated. For example, the first coefficient is equivalent to the organ's volume and the other coefficients model radial frequencies of the organ shape. The SFT coefficients can be used to find abnormalities in the shape of the organ or a section thereof.

Motion Fields (MF) Translation Estimation Function

The MF translation estimation function is designed to find global movement of a certain organ, which is depicted in the source image, or an area thereof, according to the optic-flow field. The MF translation estimation function is based on one of the segmentation map in the segmentation structure and on the optic-flow field. The output is a translation vector, which is preferably represented in an array.

The MF translation estimation function calculates a global translation of an organ or a section thereof in relation to the segmented image. The output of the MF translation estimation function is actually a weighed average of the optic-flow field, where the weighs are taken according to the segmentation map. The translation vector is preferably calculated as follows:

$$Trans = \left[\frac{\sum T_c \cdot U}{\sum T_c}, \frac{\sum T_c \cdot V}{\sum T_c}, \frac{\sum T_c \cdot W}{\sum T_c}\right]$$

In another preferred embodiment of the present invention, the calculation of the translation vector is based on a calculation of the deviation between the center-of-mass of the organ or the section thereof in the source image and in the segmented image. The center-of-mass calculation is preferably performed as described above.

Motion Field Error Estimation (MFEE) Function

The error of the optic flow process describes a deviation between the reference and source records or between respective segments thereof. Preferably, the MFEE is based on the optic flow field. Preferably, the MFEE calculates the deviations for between a number of respective segments and outputs a number of deviations, wherein each deviation is separately fed into the vector feature. Each one of the deviations serves as a feature within the feature vector. The deviation can be defined in various ways, for example by summing the squares of length of all optic flow motion field vectors.

Motion Field Divergence (MFD) Estimation Function

The MFD estimation function is designed to identify areas within the depicted source organ for which there are no corresponding areas in the reference record, or areas that have increased/decreased in volume. As the optic flow motion field divergence value is high/low in such areas, as these areas will whether disappear or emerge. The MFD estimation function performs a calculation of the divergence of the motion field in common methodology that will not be described in details here. It later finds regions in which there is a local maximum of the divergence that is beyond a certain threshold.

A Hyperdense and Hypodense Areas (HDAs) Estimation Functions

The HDA estimation function is designed to find hyperdense areas, hypodense areas, or a combination thereof in a certain organ, which is depicted in the source image, or in a section thereof. Hyperdense areas may indicate, for example, tumor, calcification or a hemorrhage, while hypodense areas may indicate other abnormalities, such as low density soft tissue, hypodense fluid, etc.

The HDA estimation function is based on the segmentation structure of the estimated organ and source image. The output is vectors of hyperdense and hypodense areas, as further described below.

Figure 10:
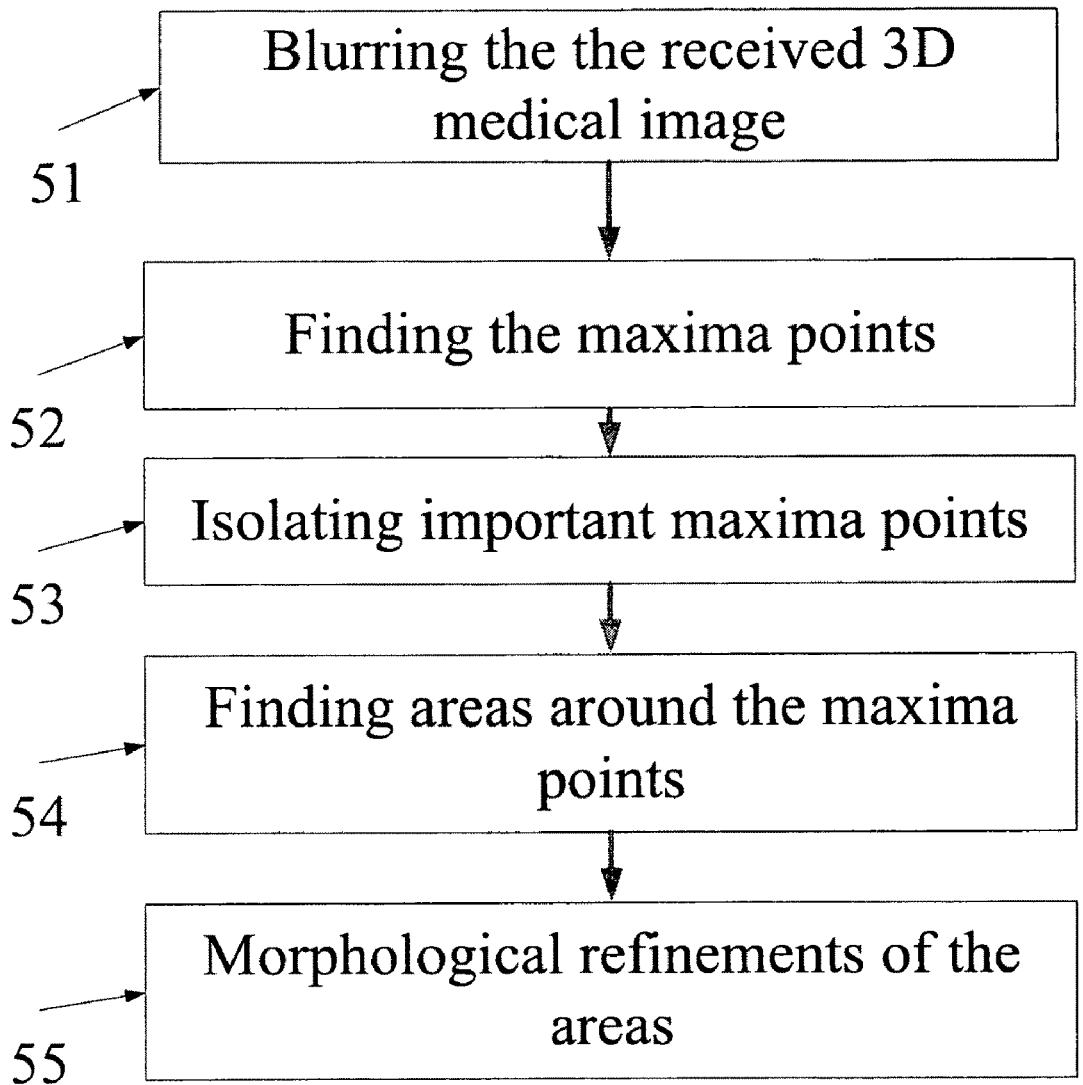
FIG. 10 is a flowchart of a method for identifying hyperdense areas in a source image, according to one preferred embodiment of the present invention.

Reference is now made to FIG. 10, which is a flowchart of a method for identifying HDAs in the source image. Such an identifying allows the evaluating of the HDAs according to predefined patterns.

During the first step, as shown at 51, a predefined filter mask is used in order to blur the source image. The predefined filter mask is preferably defined to match reference segments that may comprise HDAs. It should be noted that the blurring procedure is generally well known and therefore is not described here in greater detail Then, as shown at 52, local high/low intensity level maxima points in the source image are identified and labeled. That procedure is being performed for each segmentation mask. The procedure of finding maxima/minima points is generally well known and therefore is not described here in greater detail. During the following step, as shown at 53, important local maxima/minima points are isolated using one or more thresholds. For example, an absolute threshold, which is a threshold that delimits the values of the maxima/minima points, a neighborhood threshold, which is a neighborhood relative threshold, and a standard deviation threshold, which is an adaptive threshold that excludes maxima/minima points with high standard deviation, can be used.

Then, as shown at 54, the area around each one of the maxima/minima points is identified. Those areas can be identified using various techniques, for example, watershed, expanding active contours etc. Later, common morphological operations applied on those areas to get continues areas suspicious as hypodense or hyperdense regions. The refined vector of the maxima/minima areas is preferably outputted as a vector of HDAs.

A Symmetry Analysis (SA) Estimation Function

The SA estimation function is designed to calculate the symmetry-level between left and right organs or left and right sections of the organ that is depicted in the source image. Moreover, the SA estimation function may be used for comparing between left and right structures of a certain organ, such as the cerebellum, or between a certain organs from the source image and a respective organ from the reference image.

The SA estimation function is based on the Left and Right segmentation maps of the estimated organ and on the sampling grid. The output is a value that reflects the symmetry-level.

For clarity, VL and VR respectively denote the left and right segmentation maps, G denotes the sampling grid, (I, J, K) denote the dimensions of G, (X, Y, Z) denote the primal axes of G, and [hx', hy', hz'] are the intervals of G. The origin of G is preferably at its center.

Preferably, the left and right organs or sections thereof are sampled on separate, preferably centered, rotated grid.

In one embodiment of the present invention, the SA is performed as follows:

During the first step, a mirrored version of the VL is generated. The VL is preferably mirrored about its X-axis. Then, the center-of-mass of the VL (CL) is calculated using first order moments. In the following step, a rotation matrix of the VL (UL) is calculated using second order moments. Based on UL and VL a new rotated grid GL' is calculated as follows:

$$GL' = \{p' | p' = UL \cdot p - CL, p \in G\}$$

Subsequently or parallelly we calculate a new rotated grid GR' for the VR. In order to generate such a grid we calculate the center-of-mass of the VR (CR) is using first order moments. In the following step, a rotation matrix of the VR (UR) is calculated using second order moments. Based on UR and VE the new rotated grid GR' is calculated as follows:

$$GR' = \{p' | p' = UR \cdot p - CR, p \in G\}$$

where VR' is the sampling of VR on the new grid GR' and VL' is the sampling of VL on the new grid GL'. During the final step, an MSE comparison is performed between VR' and VL'. The outcome of the MSE comparison reflects the symmetry level.

Such a symmetry analysis can be designated to a certain organ, such as the brain.

As described above, the medical image analysis system can be used for classifying source images that depict different organs. Different organs have different characteristics and pathologies. Therefore, in order to provide better analysis of the source image, specific estimation functions, which are adjusted according to the organ that is depicted in the source image, are used. Other estimation functions can also be applied in order to extract more information from the source image, the optic-flow field, and the segmentation structure. Examples for estimation functions, which are designated to the brain, are described hereinafter:

A Curvature Based Symmetry Analysis (CBSA) Estimation Function

The CBSA estimation function is designed to classify segmented cerebrum organs as healthy or abnormal. The underlying principle is the embedding of those organs in a high dimensional feature space and applying a classification algorithm on these features. Moreover, the CBSA estimation function may be used for comparing between left and right structures of a certain organ, such as the cerebellum, or between a certain organs from the source image and a respective organ from the reference image.

The CBSA estimation function is based on the assumption that the organs are manifolds of genus 0 and therefore a conformal mapping can be found between segmented cerebrum organs and a predefined sphere.

The CBSA estimation function receives a triangulated mesh that approximates the manifold and represents an organ's surface. Preferably, the curvature, which may be Gaussian or a mean, of the underlying manifold at every vertex of the mesh is estimated. The estimation of the curvature can be estimated in a simple procedure if the mesh is regulated. Therefore, we first regularize the mesh.

Preferably, the mesh is regularized both globally and locally. By global regularization, the mesh is converted to a mesh in which every vertex has exactly the same number of neighbors. By local regularization, the mesh is converted to a mesh in which every tetrahedron, defined by the vertices PI, P2, P3, and P where the projection of P onto the face of PI, P2, and P3 coincides with the center of the face. Preferably, the regularization process is an iterative process. An initial mesh, which is located near the input surface and almost globally regulated, is used as a basis and iteratively changed toward the input surface while local regularity is enforced.

The initial mesh is the product of an iterative subdivision of a dodecahedron, see M. Hebert et al., A Spherical Representation for Recognition of Free-Form Surfaces, IEEE' PA MI, 17(7), JULY 1995 and H. Y. Shum et al., On 3D Shape Similarity, tech. report CMU-CS-95-212, Computer Science Department, Carnegie Mellon University, 1995 which are herein incorporated in their entirety by reference into the specification. Such a process yields a mesh that is almost fully regulated in the sense that apart from 12 pentagonal cells, all of its cells have six neighbors. Preferably, the iterative process is performed on a triangulation, which is the dual of the mesh. The triangulation is constructed by subdividing each triangular face of a 20-face icosahedron, which is the dual of a dodecahedron, into 2N smaller triangles. The final mesh is built by taking the dual of the 20·2N faces triangulation, yielding a mesh with the same number of nodes.

Once the initial mesh has been created, it is warped towards the input surface by applying a physical model of two forces that influence the vertices. The first one is between the vertices and their projection onto the surface. This force causes the mesh to be drawn to the surface. The other one is between the vertices and their projection onto a normal to the triangle created by their immediate neighbors and passing through its center.

Figure 11:
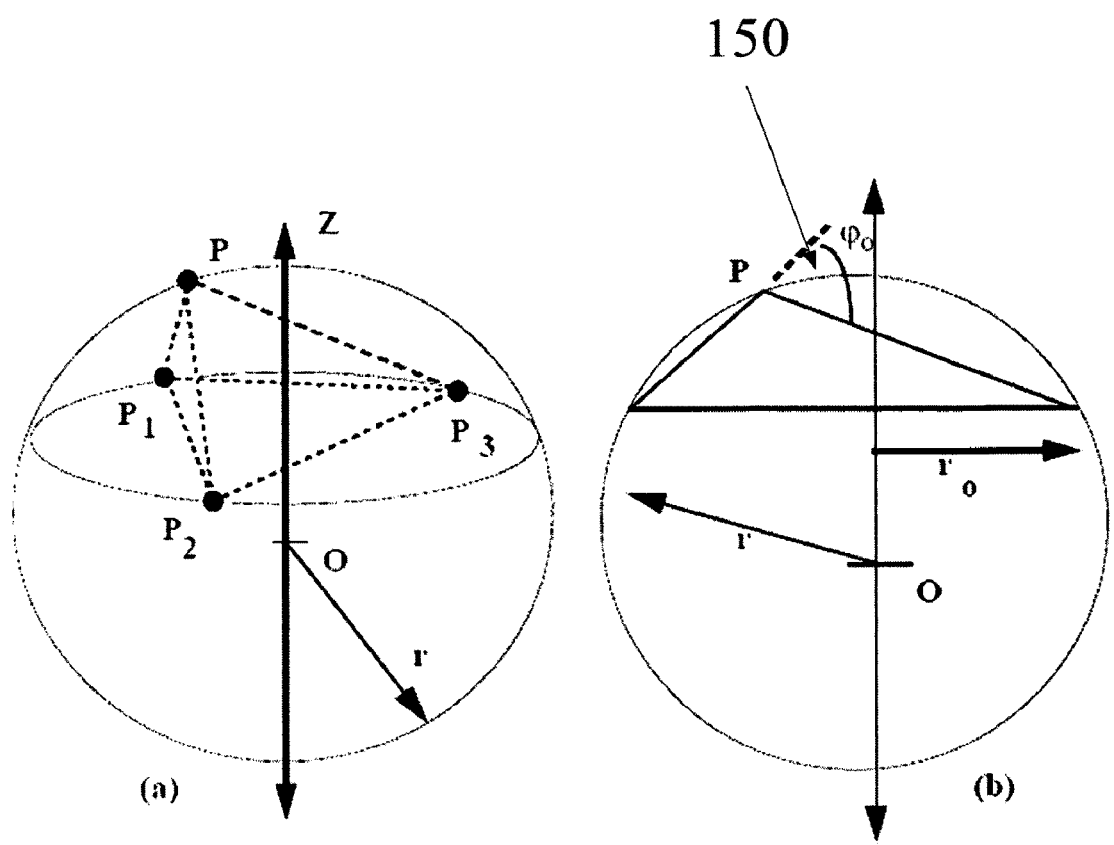
FIG. 11 is a graphical representation of a curvature approximation on a sphere, which is performed by calculating a simplex angle.

Curvature approximation is assigned to every vertex of the mesh. The approximation can be performed by standard methods, for example, by calculating the simplex angle, as shown at 150 in FIG. 11, herein incorporated in their entirety by reference into the specification. The simplex angle is defined as a function over a sphere, as shown at 151 in FIG. 11. A mesh that approximates the surface and contains information about the curvature is received after the simplex angle 150 is calculated for each one of the vertices. The mesh is mapped to a sphere by a conformal mapping; see S. Angenent et al., On the Laplace-Beltrami operator and brain surface flattening, IEEE Trans. On Medical Imaging, 18(8), August 1999 that is herein incorporated in its entirety by reference into the specification.

p denotes a selected point on the surface that is mapped into a complex plane, which is in turn further mapped to a sphere, such as Riemann's sphere, by a conformal mapping that is preferably obtained by solving a discrete approximation equation:

$$\Delta z = \left( \frac{\partial}{\partial u} + j \frac{\partial}{\partial v} \right) \delta_p$$

where $\Delta$ denotes the Laplace-Beltrami operator, (u, v) denote the conformal coordinates near p, $\delta$ denotes a Dirac Delta Function (DDF). Preferably, we solve a finite element approximation for this equation.

The final features are now used for formulating a metric among them. One feature is selected as the reference feature. The identity of the feature is not crucial as it determines only the location of the samples of the curvature function. These are assumed dense enough for a good interpolation. The distance between two final features is the mean of square distances between the curvatures measures, represented as simplex angles, on the two spheres. Preferably, a vector that comprises the distances is added to the FV. Such values can be used with a K-means algorithm to classify every incoming segmented organ as healthy or deformed. Such classification is based on a set of manually classified dataset.

A Skull Uniformity Estimation (SUE) Function

The SUE function, for example, is designed to determine if a skull, which is depicted in the source image or section thereof, is in a normal state. The SUE function is based on the source image, and on one of the segmentation maps of the segmentation structure.

In order to evaluate the normality of the skull, the uniformity of its outer and inner surfaces is estimated. Preferably, the SUE function returns a binary value that indicates whether the skull is uniform or not.

As skulls have a lot of normal sutures, holes and discontinuities, the SUE function, which is used for estimating the uniformity of the skull's external surface, has to consider such holes and discontinuities as normal.

The segmentation structure preferably comprises a reference segment that depicts the skull. Different areas of the skull depicted in the reference segment are labeled as normal sutures. During the implementation of the SUE function, fractures or suspected points are detected. The detection is done by extracting the most negative eigenvalues multiplication ($\lambda 1 \cdot \lambda 2$, as explained below). Areas as such indicate valley-like structure, which is relative to the structure of the sutures and fractures. After finding a set of suspected points we check, according to the labeled areas in the related reference segment, whether or not this point is defined as a normal suture, or another normal segment. If the area is not segmented as normal structure, we check symmetry between the right and the left sides of the skull. If suspected points which are symmetrical to the candidate point are not found, the surface of the skull is defined as not uniform.

In order to improve further the SUE function, few more steps can be taken.

Preferably, during the implementation of the SUE function the symmetry between the right and left sides of the skull's skeleton is evaluated. If the sides are not symmetrical, the surface of the skull is defined as not uniform. In one embodiment of the present invention, the symmetry level, is determined in two comparisons. During the first comparison, the lengths of the right and left skull contours, which may be referred to as the inner and outer skull contours, are compared. During the second comparison, the right and left mean and Gaussian curvatures of the skull skeleton, which may be referred to as the inner and outer mean and Gaussian curvatures of the skull skeleton, are compared. The 3D skeleton of the skull is derived as followed: First a distance map is generated by employing a re-distance function on the skull segmentation mask. Then, eigenvalues, such as $\lambda 1, \lambda 2, \lambda 3$, where $\lambda 1, > \lambda 2 > \lambda 3$ of the 3D distance map, are calculated. The skeleton is generated by taking the values of $\lambda 1$, above a certain threshold.

In order to improve further the estimation of the SUE function the radiodensity level of areas of the skull can be used. Preferably, during the implementation of the SUE function the HU values of voxels in the source image that matches labeled areas in the reference segment are evaluated in order to identify abnormities in the sutures and holes, such as widely open coronal sutures etc.

Clearly, other uniformity estimation functions, which are adapted to other organs, can be used. Such uniformity estimation functions require deferent measures to evaluate the uniformity level.

A Numerical Measurements Estimation (NME) Function

The NME function evaluates several numerical measurements that refer to normal or abnormal behavior of the brain. For example, the NME function is used to calculate the distances between the top left point and the top right point of the lateral ventricles and the right and left inner sides of the skull respectively. These distances are respectively denoted by lines "a" and "b". $\alpha$ denotes an angle between the two rooms of the brain. The angle $\alpha$ is measured from the 3D center point, such as the center of mass, of the lateral ventricles. Distances a and b, and the angle $\alpha$ can be used, either separately or with other feature documented in the FV for classifying the source image. The NME function can be used to measure numerical measurements, such as relative distances, absolute distances, and angles in many other parts of the brain. Any anchor organ in the brain can be used to determine numerical measures. For example, the NME can evaluate the distances between the lateral ventricles to the Falx. Moreover, by using numerical measurements from any central anchor point to another estimated symmetrical anchor points, we can characterize local symmetry between organs.

Cerebrospinal Fluid of the Sub-Arachnoid's Space Estimation (CSFSAE) Function

The CSFSAE function is based on the segmentation map of the CSF that is populated at the sub-arachnoid space, such as the cisterns, sulcus, and fissures. The CSFSAE function mainly performs the following:

a. Calculating the CSF volume in the sub-arachnoid space.
b. Comparing the left and right sub volumes of the CSF, according to the MSP. Preferably, the comparing is performed by verifying that the volume difference of the CSF in both sides of the brain-stem are in a certain range.
c. Verifying that the CSF is uniformly distributed in the sulci, by calculating the PDF of the CSF in that region and checking the uniformity of the PDF. PDF is constructed by generating a thickness map on the CSF by projecting a unit sphere with the center-of-mass of the CSF. This thickness map can be seen as the probability density function (PDF) of the CSF. It should be noted that various known techniques may be implied for calculating the uniformity level of the PDF, such as analyzing the Fourier coefficients of the PDF.

Organs Verification and Structure Recognition (OV-SR) Function

The OV-SR function is designed to verify the existence of typical organs in the received source image, for example in a source image that depicts the brain, and to rank to the degree of similarity of the verified organs to respective typical structures. The OV-SR function is based on the segmentation structure of the source image, and on a set of normal segmentation structures that were extracted during the training process and stored in association with a related reference record.

The OV-SR function outputs a scalar vector, which may be referred to as a verification list, to be added to the feature vector. Each scalar in the vector is related to a different organ. The value of each scalar represents similarity-measure of that organ's shape and the expected shape. The values are in the range [0,1] where 0 is given when the organ is not present in the source image and 1 is given when the organ is present and has an expected shape. In the brain, the verification list is related to, for example, various cisterns, such as the cisterna magna, the ambient cistern, the suprasellar cistern, the prepontine cistern, etc., different parts of the ventricular system, such as the temporal horns and the fourth ventricle, some of the fissures, such as the sylvian fissure, etc.

Ballooning Function

The Ballooning function is designed for determining whether a ballooning phenomenon occurred in the source image or not. Such a function can be used to estimate the probably of the existence of a blockage of the $4^{th}$ ventricle, as this blockage causes certain areas of the ventricular system to swell. The ballooning function is based on the source image, the source segmentation structure, and a list of segmentation tags describing weakness points, which are the areas where the ballooning can occur, such as the lateral ventricles.

In order to determine weather the ballooning phenomenon occurred, we first detect all the areas corresponding to the week-point tags in the source segmentation. For each such area, we check if the ballooning occurred. Such a process can be done by means of volume and curvature measurements, or by calculating the average divergence in those areas. Those measurements can be also compared to a set of normal corresponding areas generated from the database.

MSP Symmetry Estimation Function

A midsagittal plane (MSP) symmetry estimation function is designed to identify the symmetry level of the MSP. The MSP is found as the manifold separating between the left and right hemispheres. The hemispheres are found in the segmentation process. After the MSP is extracted, we measure its diversion from a plane by common means, such as total variation measurement.

Additional Optional Estimation Functions, which are Designated for the Brain, are Elaborated Hereinafter:

1. A calcification estimation function that is designed to detect calcifications in certain areas, known in advanced, and indicated by one or more of the segmentation maps. It can be done by means on color measurements, for example, looking for areas with calcification HU in the choroids-plexus segmentation mask. The output is a vector of certainty-level value to be added to the feature vector. Each value corresponds a different area in which a calcification is expected.

2. A middle ventricle estimation function. The middle ventricle is divided to two portions, each in a different hemisphere. The symmetry of the middle ventricle is evaluated by measuring the size of the portions in each one of the hemispheres.

3. A temporal horns estimation function that is designed to evaluate the distance between temporal horns from different hemispheres.

It should be noted that other characteristics of organs and sections thereof may be measured. For example, one or more of the following characteristics are estimated and added to the feature estimation vector a surface curvature, motion field rotation, a motion field deformation estimation, irregularities in the motion field, identification of abnormal structures, high-density regions, and ridges.

Reference is now made, one again, to FIG. 1. After the feature extraction module finalized the feature extraction process, the FV is generated. The segmentation and extraction unit 3 outputs the FV and forwards it to the classification unit 4. The classification unit 4 may comprise one or more of classifiers, which are used to classify the source image according to the received FV.

Preferably, the classification unit labels each source image with a priority level, a normality level, or both. Preferably, each one of these outputs is preferably assigned with a certainty level that reflects an estimation of the accuracy of the priority level, the normality level, or both. The priority level can later be used for prioritizing the source image in relation to other prioritized source images or for alarming the system user if the priority level is too high. The normality level can be used for separating a list of 3D medical images to two or more sub-lists of 3D medical images having different normality values.

The basic classifier is a normal-abnormal classifier. Based on the FV that is received from the segmentation and extraction unit 3, the classification unit 4 determines whether the organ that is depicted in the source image has one or more positive pathological indications. Such a determination may be performed in using different classifiers. In one embodiment, one or more classifiers determine the normality level of the source image according to a certain probability scheme. The probability scheme is based on one or more measures of abnormality. Preferably, two classifiers are used, wherein one of the classifiers determines a normality level and the other determines a priority level. Preferably, two classifiers are used, wherein one is used for determining a normality level and the other is used for determining an abnormality level.

Classifiers that are more complicated may be used to estimate the severity level that is reflected from the positive pathological indications in the received FV. Preferably, the classification unit 4 comprises a classifier that measures the probability that there are positive pathological indications in a given source image. Preferably, the classification unit 4 comprises a classifier that estimates the probability that there are positive pathological indications of certain pathology in the depicted organ. Preferably, the outputs of the classifiers are forwarded to the diagnosis unit.

It should be noted that the number of used classifiers is not limited. Different classifiers may be added to the system according to different criteria or combination thereof. The FV comprises varied and comprehensive information about positive and negative pathological indications of different areas of the organ that is depicted in the related source image. As such, different classifiers, which are defined according to experts' definitions, may be used. Preferably, one or more of the classifiers are used for diagnosing a combination of the features and determining based thereupon a priority level. Preferably, each feature is multiplied by a predefined probability factor.

Preferably, the classification unit 4 comprises an alerting module that is designed to alarm the system user when one or more of the classifiers classify the source image as having a priority level above a predefined threshold. The alerting module may be used for alerting the user by automatically sending an email or any other electronic message, to a designated electronic address or for presenting a pop-up window on a display device that is connected to the system. When such an embodiment is used, the medical image analysis system 1 can alert the user on real time whenever a critical pathological indication has been identified in one of the received source images. Such an embodiment increases the effectiveness of a therapy given to patients as it alarms the system user regarding a pathological indication immediately after the source image has been acquired by the medical imaging system.

Figure 12:
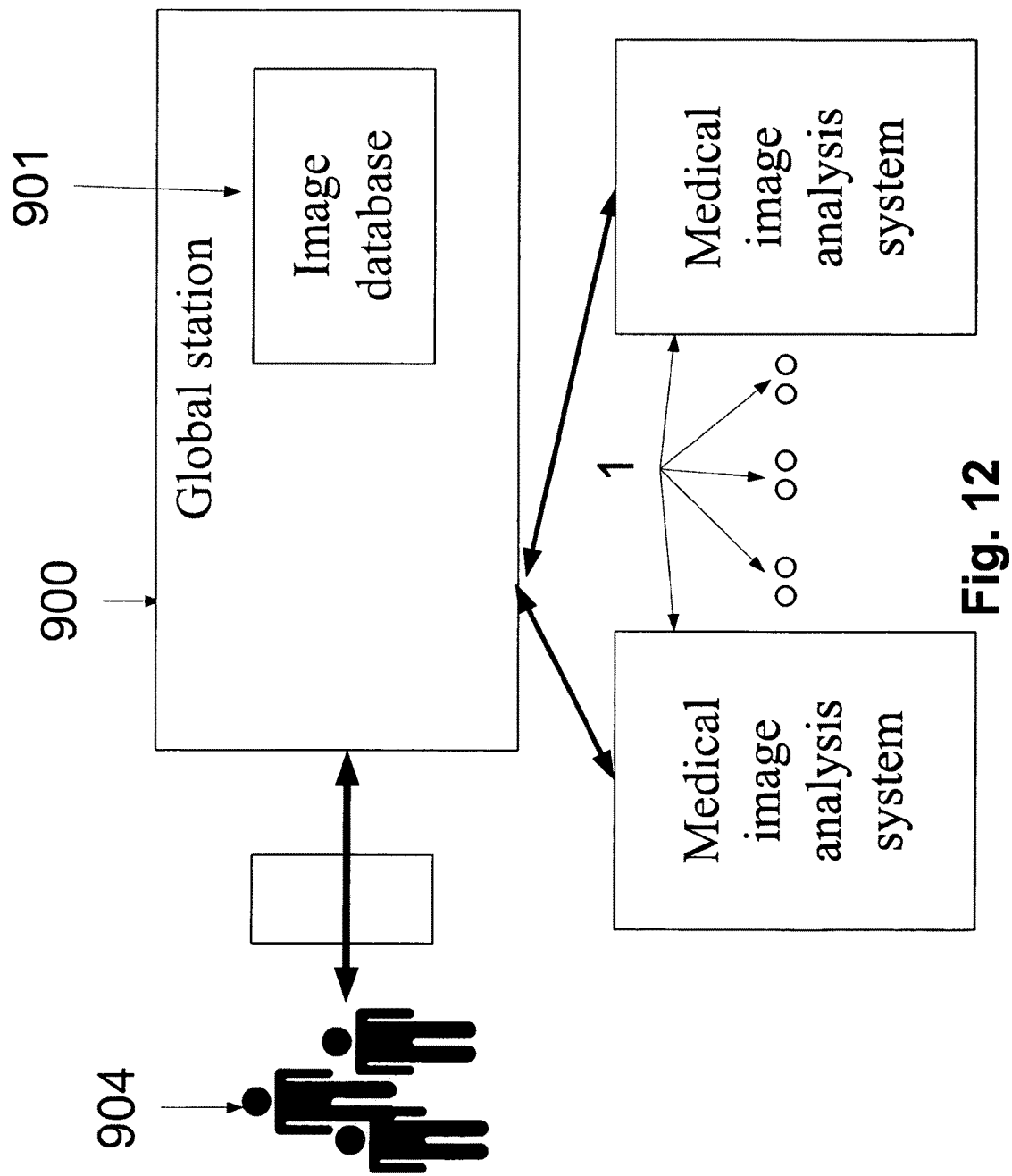
FIG. 12 is a schematic illustration of an arrangement of a number of medical image analysis systems, a global station with an image database, and a team of experts, according to a preferred embodiment of present invention.

Reference is now made to FIG. 12, which is a schematic illustration of an arrangement of a number of medical image analysis systems 1, each as depicted in FIG. 1, a global station 900 with an image database 901, and a team of experts, according to one embodiment of present invention. In one preferred embodiment, the medical image analysis systems 1 function as workstations which are connected to the global station via a computer network. In such an embodiment, the medical image analysis systems 1 are posted in a number of remotely located radiology centers.

The global station 900 function as a central station that allows a continuous development of the aforementioned reference records, feature extraction functions, and classifiers, inter alia by allowing a team of experts 904 to configure them and by applying a learning scheme. In one embodiment of the present invention, the global station comprises a database of accurately defined malignancies and other pathological indications. The database is constantly growing with additional 3D medical images and related diagnoses from different local stations and experts.

The database is used for generating new classifiers, and reference records. The database is preferably built using training set and a learning mechanism. During the learning process, the global station uses an FV that has been generated according to a certain source image as the input vector of the training set and a related experts' diagnosis is used as the answer vector of the training set. Preferably, a source image, a related feature vector, and a related diagnosis may be received at the global station from one of the medical image analysis systems 1, where the related feature vector is used as the input vector of the training set and the related diagnosis is used as the answer vector. In such an embodiment, the aforementioned certainty level of the evaluated source image may be variable as the level of expertise of the radiologist that has provided the diagnosis may not be uniform. Preferably, by default certainty level of evaluated source images which are received from one of the medical image analysis systems 1 is low.

For example, if the source image depicts a brain, the diagnosis is of one or more expert neuroradiologists that define the pathological indications in the source image and areas thereof. The diagnosis may comprise neuroradiology indications such as an identification of a tumor and the determination whether it is malignant or benign, a brain atrophy level, an identification of a brain stroke, an identification of a cerebrovascular accident (CVA), polipisis, etmoeditis, Sinusitis, enlargement of Brain ventricles, cyst, and metastases.

The input and answer vectors are used together with a supervised learning method to train the image database 901. Supervised learning methods are generally well known and therefore are not described here in greater detail. The classifiers can be implemented one of the known machine learning algorithms, for example decision trees, support vector machine (SVM), neural networks, K-nearest neighbors (KNN), with boosting (i.e., AdaBoost).

Preferably, classifiers are built according to the output of the training set and one or more machine leaning algorithms, as described below.

As depicted in FIG. 12, the global station 900 is connected to one or more of the aforementioned medical image analysis systems. Each system functions as a workstation that improves the workflow of one or more radiologists and the accuracy of the diagnosis thereof, as described above. The interaction between the global station 900 and the workstations 1 is established over a network connection, such as the Internet.

The image database is designed to grow constantly by new source images, which are fed either directly by the expert team 904 or via the workstations 1, as described above. As such, the image database 901 is used to generate new classifiers and reference records. A new classifier is preferably generated according the following steps:
1. The new classifiers are based on the source images, which are stored in the image database. For each source image in the image database 901, an FV is generated by applying one or more feature extraction functions, preferably using the medical image analysis system 1, as described above. Preferably, each source image is associated with a related diagnosis that has been provided by the team of experts 904.
2. Each one of the FV is inserted, together with the associated diagnosis, into a learning machine such as a support vector machine (SVM), a neural network, a decision trees-based module, etc.
3. The learning machine generates a new classifier according to the received FV.
4. The new classifier is added to the memory of the medical image analysis system 1.

Preferably, as the group of experts 904 has access to image database, they can constantly develop additional feature extraction algorithms and classifiers and to enhance the existing ones.

Figure 13:
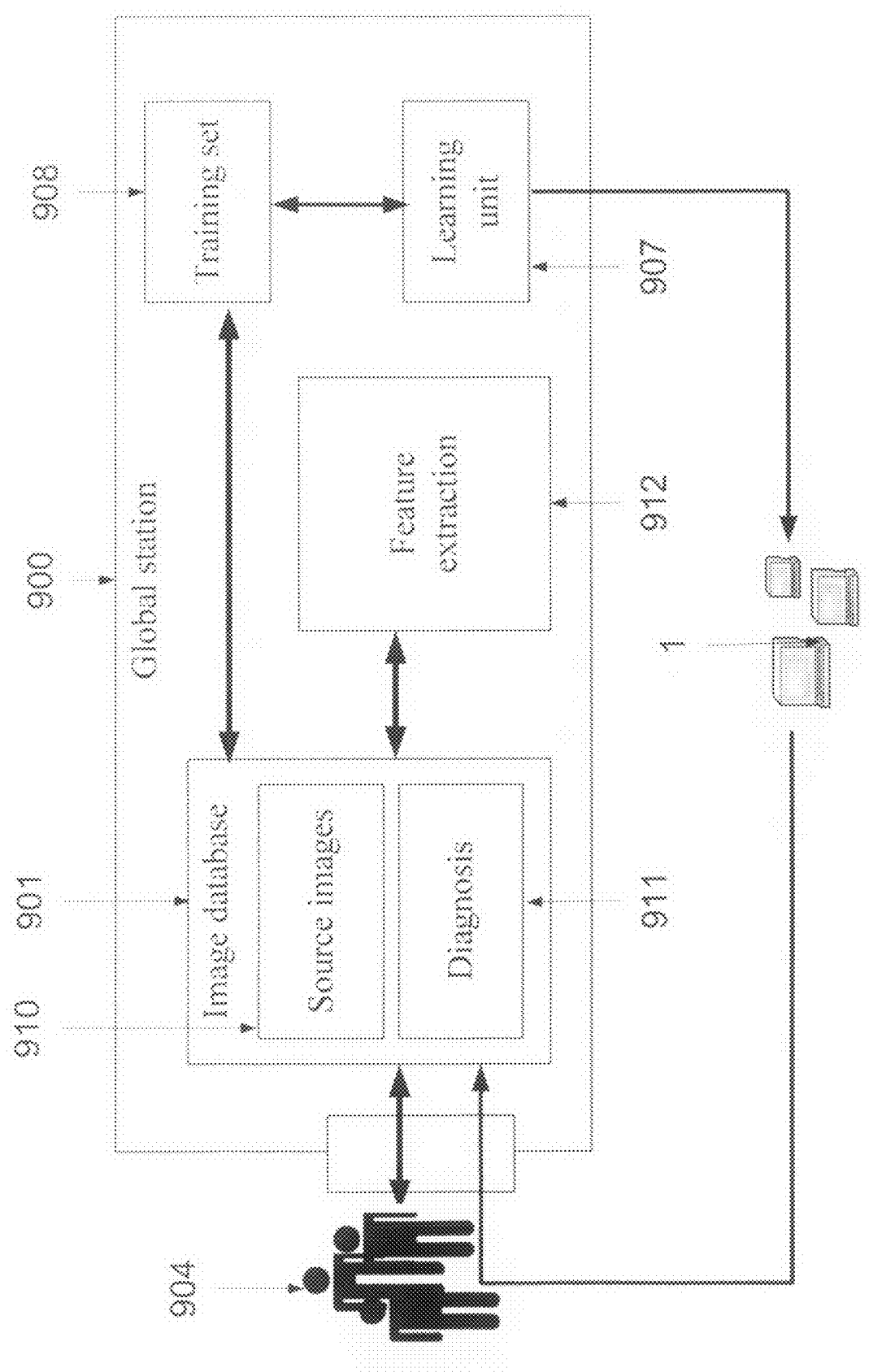
FIG. 13 is a schematic illustration the global station of FIG. 12, according to a preferred embodiment of present invention.

Reference is now made to FIG. 13, which is a schematic illustration of the global station 900 that is depicted in FIG. 12 and the connections thereof to the workstations 1 and to the team of experts, according to a preferred embodiment of present invention. The image database 901, the group of experts 904, and the workstations 1 are as depicted in FIG. 12, however FIG. 13 further depicts the aforementioned training set 908 and the learning mechanism 907, which are used for allowing the generation of new classifiers according to knowledge accumulated in the image database 901, as described above. The image database 901 stores the source images 910 and related diagnosis, which are associated, as described above.

The global station 900 allows top down knowledge sharing by sending the outputs of the learning unit 907 to the workstations 906, thereby allowing users to access improved or new classifiers, feature extraction functions, etc.

The depicted global station 900 further allows bottom up knowledge sharing as the workstations 906 allows physicians and teams of experts to upload source images and diagnoses thereof to the image database. Preferably, source images with low certainly level are labeled and uploaded automatically to the global station. Such an embodiment allows a fast automatic detection of weak spots of the system. Preferably, the uploaded source images are further attached with export's diagnosis from the group of experts 904.

Preferably, the classification unit 4 associates a priority level to the source image.

Preferably, the global station 900 comprises a feature extraction module 912 that generates the FV that is forwarded to the training set 908 by applying the aforementioned FE algorithms on a related source image and preferably combining medical information about the patient.

Figure 14:
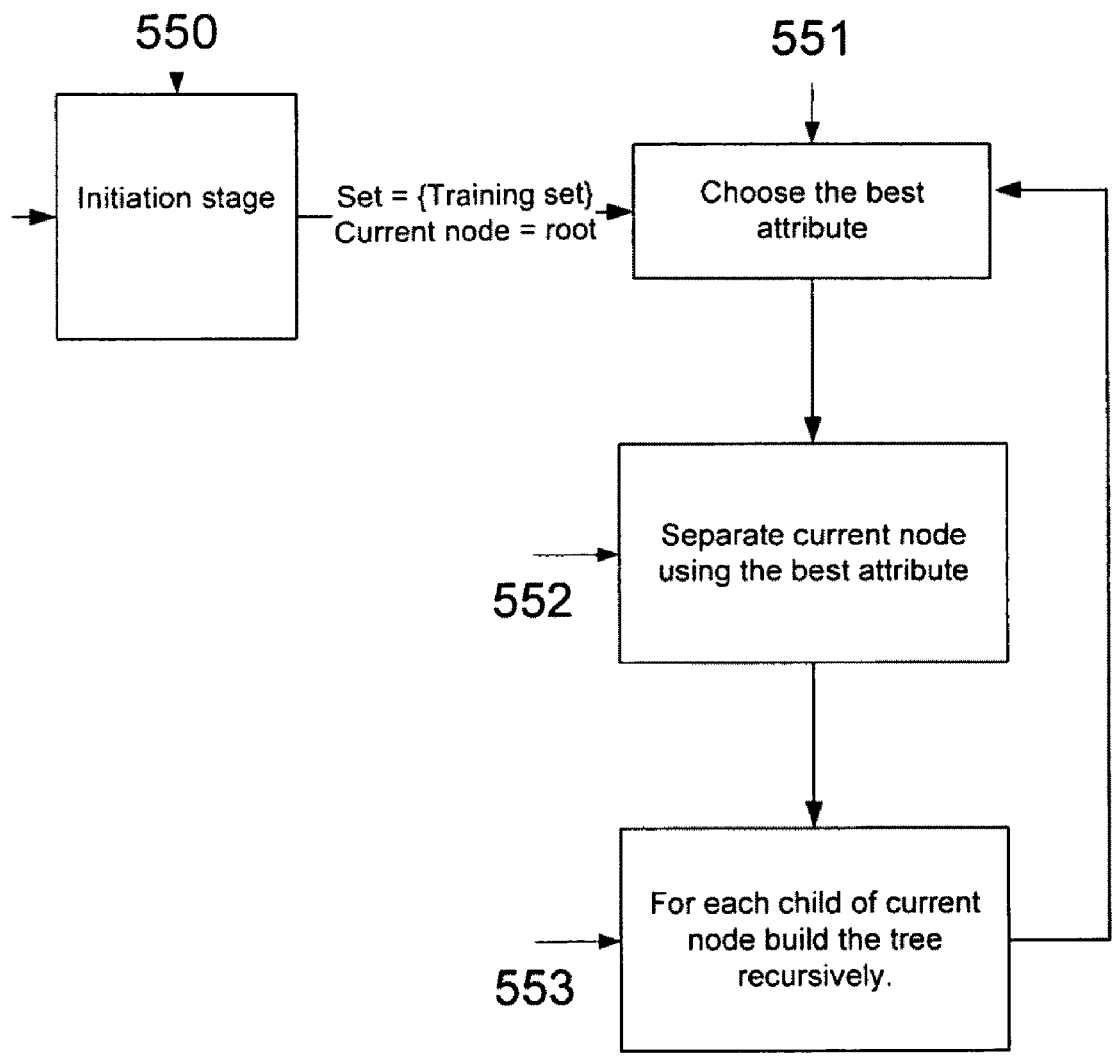
FIG. 14 is a flowchart of an iterative dichotomiser 3 (ID3) algorithm for building a decision tree based on a training set, according to one embodiment of the present invention.

There more than one way to build classifiers from training sets, for example, using a decision tree. Reference in now made to FIG. 14, which is a flowchart of an iterative dichotomiser 3 (ID3) algorithm for building a decision tree based on the training set, according to one embodiment of the present invention. During the first step, as shown at 550, the training set and the current node are initialized. Then, as shown at 551, the best attribute is chosen, preferably as the attribute with the maximal gain. Preferably, the gain is defined according to the following equation:

$$\text{Gain}(A) = I(p, n) - R(A)$$
$$R(A) = \sum_i \frac{p_i + n_i}{p + n} I(p_i, n_i)$$

Where A denotes a given attribute, p and s denotes portions of a set of attributes S in which p represents (+1) and n represents (−1), and $p_i$, $n_i$ are the examples remaining after separating the S using A. I(p,n) denote the following calculation:

$$I(p, n) = -\frac{p}{p+n}\log_2\frac{p}{p+n} - \frac{n}{p+n}\log_2\frac{n}{p+n}$$

where I(p, n) is the information contents of S. During each iteration, the best attribute is chosen and the set is divided based on that attribute. In particular, as shown at 552, the current node is separated using the best attribute. After the current node is separated, as shown at 553, a tree is built recursively for each one of its children nodes. The process of recursively constructing a decision tree is generally well known and therefore is not described here in greater detail.

It is expected that during the life of this patent many relevant apparatuses and systems will be developed and the scope of the terms herein, particularly of the terms source image, reference image, database, an feature extraction function are intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for analyzing a source medical image of a body organ, said system comprising:
   a) an input unit for obtaining the source medical image, the source medical image having at least three dimensions;
   b) a segmentation unit, operatively associated with said input unit, configured for segmenting the source medical image into a segmented source medical image by matching the source medical image with a reference medical image of a respective normal organ, said segmented source medical image including a plurality of source segments, said reference medical image already being segmented into a plurality of reference segments, said reference medical image having at least three dimensions;
   c) a feature extraction unit, operatively associated with said segmentation unit, configured for obtaining a plurality of features of the body organ from the segmented source medical image; and
   d) a pathology detector unit, operatively associated with said feature extraction unit, configured for indicating at least one pathology based on said plurality of features.

2. The system of claim 1, wherein the body organ is a brain.

3. The system of claim 2, wherein at least one of said features is calculated according to the uniformity of a skull that being depicted in the source medical image.

4. The system of claim 2, wherein at least one of said features is calculated according to the ratio between the measures of ventricles depicted in the source medical image.

5. The system of claim 2, wherein at least one of said features is calculated according to the volume of a cerebrospinal fluid (CSF) in an upper temple depicted in the source medical image.

6. The system of claim 2, wherein at least one of said features is calculated according a minimum mean square error between said reference image and the source medical images.

7. The system of claim 2, wherein at least one of said features is calculated according an estimation of cerebrospinal fluid of in a sub-arachnoid's space in said depicted human brain.

8. The system of claim 2, wherein at least one of said features is calculated according to the positioning of a middle symmetry line that bisects said depicted human brain.

9. The system of claim 8, wherein said symmetry is based on the symmetry level of an MSP.

10. The system of claim 8, wherein at least one of said features is calculated according to a symmetry value, said symmetry value being calculated by measuring the size of at least one portion of at least one hemisphere depicted in the source medical image.

11. The system of claim 2, wherein at least one of said features is calculated according to a distance between at least two temporal horns depicted in the source medical image.

12. The system of claim 1, wherein each of said plurality of reference segments includes a collection of normative values for said features.

13. The system of claim 12, wherein each of said plurality of source segments has at least one associated normative value.

14. The system of claim 13, wherein said features include at least four different features.

15. The system of claim 12, wherein at least one of said features is selected from the group comprising features that are:
   (a) calculated according to the volume of an area of the body organ in relation to a respective volume of a respective area in said respective normal organ;
   (b) calculated according to the center-of-mass of an area of the body organ in relation to a respective center-of-mass in a respective area in said respective normal organ;
   (c) calculated according to second order moments of an area of the body organ;
   (d) calculated according to the surface area of an area of the body organ in relation to a respective surface area in a respective area in said respective normal organ;
   (e) calculated according to the average color of voxels in an area of the body organ;
   (f) calculated according to one or more characteristics of the shape of an area of the body organ in relation to a respective one or more characteristics of the shape of a respective area in said respective normal organ;
   (g) calculated according to the global motion in an area of the body organ in relation to the positioning of said respective normal organ;
   (h) calculated according to hyperdense/hypodense areas in an area of the body organ;
   (i) calculated according to the symmetry between at least two areas of the body organ; and (j) calculated according to a mean color of at least one area in the source medical image.

16. The system of claim 15, wherein said one or more characteristics are estimated according to a spherical Fourier transform.

17. The system of claim 15, wherein said one or more characteristics are estimated according to a predefined curvature.

18. The system of claim 1, wherein at least some of said features relate to a symmetry of the body organ and at least one of said features relates to non-symmetry of the body organ.

19. The system of claim 1, further comprising a registration module being configured for performing a spatial image registration according to spatial positioning differences between the body organ and said respective normal organ, said spatial positioning differences being used by said segmentation unit for said segmenting.

20. The system of claim 19, wherein said registration module comprises a global motion sub-module being configured for estimating a global motion vector according to said spatial positioning differences, said global motion vector being used during said spatial image registration.

21. The system of claim 19, wherein said registration module comprises a 3D affine transformation sub-module being configured for estimating an affine transformation vector according to said spatial positioning differences, said affine transformation vector being used during said spatial image registration and wherein said reference medical image is associated with a plurality of reference descriptors, said 3D affine transformation sub-module being configured for identifying a plurality of source descriptors in the source medical image said, said spatial positioning differences being determined according to spatial positioning differences between said reference and source descriptors.

22. The system of claim 21, wherein said reference descriptors and said source descriptors are local extrema voxels in said reference medical image and the source medical image respectively.

23. The system of claim 19, wherein said registration module comprises an optic flow sub-module, wherein said optic flow sub-module is configured for estimating a spatial optic-flow field according to said spatial positioning differences, said optic-flow field being used during said spatial image registration.

24. The system of claim 1, wherein said segmentation unit generates said plurality of source segments by matching voxels of said reference medical image with voxels of the source medical image.

25. The system of claim 1, wherein said plurality of source segments are used for identifying said plurality of features.

26. The system of claim 1, further comprising an active contour (AC) module, said segmentation unit being configured to forward said plurality of source segments to said AC module, said AC module being configured to refine said plurality of source segments according to the source medical image.

27. The system of claim 26, wherein said refinement is performed according to the Hounsfield unit (HU) values of voxels of said plurality of source segments.

28. The system of claim 1, wherein the body organ is a depicted human brain which is segmented according to two or more of: white matter, gray matter lateral ventricles, caudate nucleus, internal capsule, thalamus, lentiform nucleaus, sylvian fissure.

29. The system of claim 1, wherein at least one of said features is calculated according to the existence of predefined structures in said segmented source medical image, said existence is determined by matching segments of said segmented source medical image with a set of normal segmentation structures.

30. The system of claim 1, wherein at least one of said features is calculated according a distance between segments in said segmented source medical image.

31. The system of claim 1, comprising a classification unit which further comprises a diagnosis module, said diagnosis module being configured for generating a diagnosis report according to said features and said pathology detector.

32. The system of claim 1, comprising a classification unit comprises at least one classifier, said at least one classifier being configured to classify the source medical image according to said features, said classification being determined according to said at least one classifier.

33. The system according to claim 1, wherein said pathology detector analyses a vector including a plurality of features, and wherein said detector includes a memory storing therein a plurality of matches between vectors and abnormal situations.

34. The system according to claim 1, wherein said pathology detector aggregates a plurality of features into a single aggregate feature.

35. The system according to claim 1, wherein said features includes two or more of a HU density related property, a statistical scattering property of the HU density, a geometrical characteristic, a symmetry characteristic, a geometrical relation between different structures.

36. The system according to claim 1, wherein said pathology detector includes a collection of features and normative values for each segment of said.

37. A method for analyzing a source medical image of a body organ, said method comprising:
 a) receiving the source medical image;
 b) segmenting the source medical image into a segmented source medical image by matching the source medical image with a reference medical image of a respective normal organ, said segmented source medical image including a plurality of source segments, said reference medical image already being segmented into a plurality of reference segments;
 c) obtaining information about features in the body organ from said segmented source medical image; and
 d) detecting at least one deviation from normality in the body organ based on said features.

* * * * *